United States Patent
Suzuki et al.

(10) Patent No.: US 6,455,720 B1
(45) Date of Patent: Sep. 24, 2002

(54) 2,2(DIARLYL)VINYLPHOSPHINE COMPOUND, PALLADIUM CATALYST THEREOF, AND PROCESS FOR PRODUCING ARYLAMINE, DIARYL, OR ARYLALKYNE WITH THE CATALYST

(75) Inventors: Ken Suzuki; Tohru Kobayashi; Takenobu Nishikawa; Yoji Hori; Toshimitsu Hagiwara, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/891,304

(22) Filed: Jun. 27, 2001

(30) Foreign Application Priority Data

Jun. 28, 2000 (JP) ......................... 2000-194690

(51) Int. Cl.⁷ ................................. C07F 9/50
(52) U.S. Cl. ................. 556/21; 568/17; 568/8; 564/305; 502/162
(58) Field of Search ................. 568/8, 17, 16; 556/13, 21, 136; 564/305, 386; 502/162

(56) References Cited

U.S. PATENT DOCUMENTS

| | | | |
|---|---|---|---|
| 3,010,999 A | * 11/1961 | Garner | |
| 3,355,439 A | * 11/1967 | Welch et al. | |
| 3,422,079 A | * 1/1969 | Welch et al. | |
| 3,517,042 A | * 6/1970 | Peterson | |
| 3,634,518 A | * 1/1972 | Buddrus et al. | |
| 3,919,325 A | * 11/1975 | Bogdanovic | |
| 5,250,736 A | * 10/1993 | Michlethwaite et al. | |
| 5,510,554 A | 4/1996 | Regnat et al. | 585/466 |
| 5,576,460 A | 11/1996 | Buchwald et al. | 564/386 |
| 5,929,281 A | 7/1999 | Nishiyama et al. | 564/386 |
| 6,307,087 B1 | 10/2001 | Buchwald et al. | 558/388 |

FOREIGN PATENT DOCUMENTS

| | | |
|---|---|---|
| EP | 802 173 | 10/1997 |
| JP | 61022034 | 1/1986 |
| WO | WO 2000 02887 | 1/2000 |

OTHER PUBLICATIONS

CA:68:59654 abs of J Org. Chem. by Peterson 33(2) pp 780–4 1968.*
CA:120:245289 abs of Synthesis by Hafner et al. 12 pp 1257–52 1993.*
CA:113:212125 abs of Zh. Obshch. Khim. by Barsegyan et al 1990 60(5) pp 977–83.*
Chow, et al., "A Highly Selective Synthesis of Diarylethynes and Their . . . ", J. Org. Chem., vol. 66 (2001), pp. 1910–1913.
Nishihara, et al., "Coupling Reactions of Alkynylsilanes Mediated by a Cu(I) Salt: . . . ", J. Org. Chem., vol. 65 (2000), pp. 1780–1787).

Nguefack, et al., "An Efficient Palladium–Catalysed Coupling of Terminal . . . ", Tetrahedron Letters, vol. 37, No. 31 (1996), pp. 5527–5530.
Zim, et al., "PdCl$_2$(SEt$_2$)$_2$ and Pd(OAc)$_2$: Simple and Efficient . . . ", Tetrahedron Letters, vol. 41 (2000), pp. 8199–8202.
Miyaura, et al., "Palladium–Catalyzed Cross–Coupling Reactions of . . . ", Chem. Rev., vol. 95 (1995), pp. 2457–2483.
Bumagin, et al., "Catalytic Coupling of Terminal Acetylenes . . . ", Tetrahedron Letters, vol. 37, No. 6 (1996), pp. 897–900.
Littke, et al., "Versatile Catalysts for the Suzuki Cross–Coupling of . . . ", J. Am Chem., vol. 122 (2000), pp. 4020–4028.
Wolfe, et al., "Simple, Efficient Catalyst System . . . ", J. Org. Chem., vol. 65 (2000), pp. 1158–1174.
Tsuji, et al., Palladium Reagents and Catalysts (1995), pp. 125–88 and pp. 290–340.
Barsegyan, et al., "Interaction of tertiary phosphines with . . . ", Journal of General Chemistry USSR, vol. 60, No. 5 (1990), pp. 859–864, XP002176588.

* cited by examiner

Primary Examiner—Jean F. Vollano
(74) Attorney, Agent, or Firm—Fitzpatrick, Cella, Harper & Scinto

(57) ABSTRACT

A novel 2,2-(diaryl)vinylphosphine compound represented by the following general formula (1):

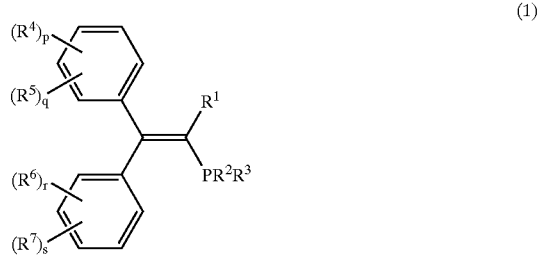

(1)

(wherein $R^1$ is a hydrogen atom, an alkyl group having 1 to 6 carbon atoms, an alicyclic group having 5 to 7 carbon atoms, etc.; $R^2$, $R^3$, $R^4$, $R^5$, $R^6$, and $R^7$ may be the same or different and each is an alkyl group having 1 to 6 carbon atoms, an alicyclic group having 5 to 7 carbon atoms, etc., provided that $R^4$ and $R^5$ taken together and/or $R^6$ and $R^7$ taken together may represent a fused benzene ring, a substituted fused benzene ring, a trimethylene group, etc.; and p, q, r, and s each is 0 to 5, provided that p+q and r+s each is in the range of from 0 to 5); a palladium-phosphine catalyst obtained by causing a palladium compound to act on the novel 2,2-(diaryl)vinylphosphine compound; and a process for obtaining an arylamine, a diaryl and an arylalkyne in the presence of the palladium-phosphine catalyst.

20 Claims, No Drawings

2,2(DIARLYL)VINYLPHOSPHINE COMPOUND, PALLADIUM CATALYST THEREOF, AND PROCESS FOR PRODUCING ARYLAMINE, DIARYL, OR ARYLALKYNE WITH THE CATALYST

FIELD OF THE INVENTION

The present invention relates to a novel 2,2-(diaryl) vinylphosphine compound and a palladium-phosphine catalyst obtained by causing a palladium compound to act on the 2,2-(diaryl)vinylphosphine compound. The invention further relates to a process for obtaining an arylamine, a diaryl and an arylalkyne in the presence of the palladium-phosphine catalyst.

BACKGROUND ART

Many transition metal complexes have conventionally been used as catalysts for organic synthesis reactions. Phosphine compounds play an extremely important role as ligands required of these catalysts. For example, in Tsuji-Trost reaction, in which an allyl compound reacts with a nucleating agent with the aid of a palladium catalyst, phosphine compounds including triphenylphosphine function to stabilize the catalyst and accelerate the reaction (see Jiro Tsuji, *Palladium Reagents and Catalysts*, JOHN WILEY & SONS, 1995, pp. 125–188, pp. 290–340).

In recent years, S. L. Buchwald et al. disclosed a method for synthesizing an arylamine by the amination reaction of an aryl compound having a leaving group (see U.S. Pat. No. 5,576,460, International Publication 2000/02887, and S.L. Buchwald et al., *J. Org. Chem.*, 2000, 65, pp. 1158–1174). Also disclosed is a process for arylamine production which is characterized by using a catalyst comprising a trialkylphosphine and a palladium compound (see JP-A-10-139742). (The term "JP-A" as used herein means an "unexamined published Japanese patent application".)

Also disclosed is a method for synthesizing a diaryl compound by the carbon-carbon bond formation reaction of an aryl compound having a leaving group with an arylboric acid compound or an arylborate ester compound (see A. F. Littke et al., *J. Am. Chem. Soc.*, 2000, 122, pp. 4020–4028, D. Z. Adriano et al., *Tetrahedron Letters*, 2000, 41, pp. 8199–8202, and N. Miyaura and A. Suzuki, *Chem. Rev.*, 1995, 95, pp. 2457–2483).

Furthermore disclosed is a method for synthesizing an arylalkyne by the carbon-carbon bond formation reaction of an aryl compound having a leaving group with an alkyne compound (see H-F. Chow et al., *J. Org. Chem.*, 2001, 66, pp. 1910–1913, Y. Nishihara et al., *J. Org. Chem.*, 2000, 65, pp. 1780–1787, J-F. Nguefack et al., *Tetrahedron Letters*, 1996, 37, pp. 5527–5530, and N. A. Bumagin et al., *Tetrahedron Letters*, 1996, 37, pp. 897–900).

Although it is important to constitute an optimal catalyst according to the intended reaction or the substrate to be reacted, there can be a variety of complicated combinations of catalyst components, i.e., a metal and a phosphine ligand. Consequently, there are cases where even when phosphine ligands which have been developed so far are used, the catalysts are insufficient in catalytic activity, etc. and hence pose a problem when subjected to practical use in industrial reactions. It is therefore important to develop a novel phosphine ligand.

An object of the invention is to provide a novel ligand useful in various catalytic reactions. Another object of the invention is to provide a process for producing an arylamine, a diaryl and an arylalkyne important as an intermediate for medicines and agricultural chemicals and as an organic electronic material using a catalyst containing the ligand.

SUMMARY OF THE INVENTION

In order to achieve the above objects, the present inventors made extensive studies. As a result, it has been found that a novel 2,2-(diaryl)vinylphosphine compound. Furthermore, it has been found that a catalyst prepared from this 2,2-(diaryl)vinylphosphine compound and a palladium compound is effective in the amination reaction of an aryl compound having a leaving group, the carbon-carbon bond formation reaction of an aryl compound having a leaving group with an arylboric acid compound or an arylborate ester compound, and the carbon-carbon bond formation reaction of an aryl compound having a leaving group with an alkyne compound, and enables an arylamine, a diaryl and an arylalkyne to be produced efficiently in a short time period. The invention has been completed based on this finding.

The invention includes the following.

1. A 2,2-(diaryl)vinylphosphine compound represented by the following general formula (1):

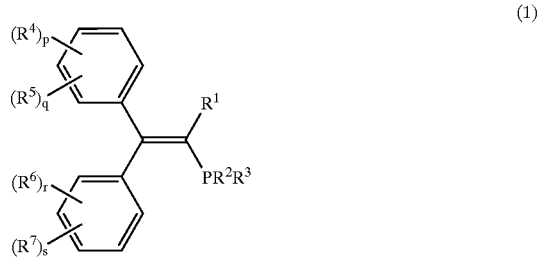

(wherein $R^1$ is a hydrogen atom, an alkyl group having 1 to 6 carbon atoms, an alicyclic group having 5 to 7 carbon atoms, or a phenyl group which may have one or more substituents; $R^2$ and $R^3$ may be the same or different and each is an alkyl group having 1 to 6 carbon atoms, an alicyclic group having 5 to 7 carbon atoms, or a phenyl group which may have one or more substituents; $R^4$, $R^5$, $R^6$, and $R^7$ may be the same or different and each is an alkyl group having 1 to 6 carbon atoms, an alicyclic group having 5 to 7 carbon atoms, a phenyl group which may have one or more substituents, an alkoxy group having 1 to 6 carbon atoms, a dialkylamino group having 1 to 3 carbon atoms, a halogen atom, a benzyl group, a naphthyl group, or a halogen-substituted lower alkyl group having 1 or 2 carbon atoms, provided that $R^4$ and $R^5$ taken together and/or $R^6$ and $R^7$ taken together may represent a fused benzene ring, a substituted fused benzene ring, a trimethylene group, a tetramethylene group, or a methylenedioxy group; and p, q, r, and s each is 0 to 5, provided that p+q and r+s each is in the range of from 0 to 5).

2. A palladium-phosphine catalyst obtained by causing a palladium compound to act on the 2,2-(diaryl) vinylphosphine compound described in 1 above.

3. The palladium-phosphine catalyst described in 2 above wherein the palladium compound is a salt or complex of palladium having a valence of 4, 2, or 0.

4. A process for producing an arylamine which comprises using the palladium-phosphine catalyst described in 2 or 3 above in the amination reaction of an aryl compound represented by the following general formula (2):

$$ArX^1 \qquad (2)$$

(wherein Ar is an aryl group which may have one or more substituents, or a heteroaryl group which may have one or more substituents; and $X^1$ is a halogen atom, a trifluoromethanesulfonyloxy group, a methanesulfonyloxy group, or a toluenesulfonyloxy group) with an amine compound in the presence of a base.

5. A process for producing a diaryl which comprises using the palladium-phosphine catalyst described in 2 or 3 above in the carbon-carbon bond formation reaction of an aryl compound represented by the following general formula (2)

$$ArX^1 \qquad (2)$$

(wherein Ar and $X^1$ have the same meanings as defined above with an arylboric acid compound or an arylborate ester compound in the presence of a base).

6. A process for producing an arylalkyne which comprises using the palladium-phosphine catalyst described in 2 or 3 above in the carbon-carbon bond formation reaction of an aryl compound represented by the following general formula (2)

$$ArX^1 \qquad (2)$$

(wherein Ar and $X^1$ have the same meanings as defined above with an alkyne compound in the presence of a base).

DETAILED DESCRIPTION OF THE INVENTION

The invention will be explained below in detail.

In the compound (1) of the invention, $R^1$ is a hydrogen atom, an alkyl group having 1 to 6 carbon atoms, an alicyclic group having 5 to 7 carbon atoms, or a phenyl group which may have one or more substituents. $R^1$ is preferably a hydrogen atom, a lower alkyl group having 1 to 3 carbon atoms, an alicyclic group having 6 carbon atoms, or a phenyl group.

Specific examples of $R^1$ include a hydrogen atom; an alkyl group having 1 to 6 carbon atoms, such as methyl, ethyl, propyl, isopropyl, n-butyl, tert-butyl, isobutyl, sec-butyl, pentyl, or hexyl; an alicyclic group having 5 to 7 carbon atoms, such as cyclopentyl, cyclohexyl or cycloheptyl; a phenyl group which may have one or more substitutents, for example, a lower alkyl group having 1 to 4 carbon atoms, such as methyl, ethyl, propyl, isopropyl, n-butyl, tert-butyl, isobutyl or sec-butyl, a lower alkoxy group having 1 to 4 carbon atoms, such as methoxy, ethoxy, propoxy or butoxy, a di(lower alkyl)amino group in which each alkyl has 1 to 3 carbon atoms, such as dimethylamino, diethylamino or dipropylamino, or a halogen atom such as fluorine, chlorine, bromine or iodine.

$R^2$ and $R^3$ may be the same or different and each is an alkyl group having 1 to 6 carbon atoms, an alicyclic group having 5 to 7 carbon atoms, or a phenyl group which may have one or more substituents. Preferably, $R^2$ and $R^3$ may be the same and different and each is a lower alkyl group having 1 to 4 carbon atoms, an alicyclic group having 6 carbon atoms, or a phenyl group.

Specific examples of $R^2$ and $R^3$ include an alkyl group having 1 to 6 carbon atoms, such as methyl, ethyl, propyl, isopropyl, n-butyl, tert-butyl, isobutyl, sec-butyl, pentyl or hexyl; an alicyclic group having 5 to 7 carbon atoms, such as cyclopentyl, cyclohexyl or cycloheptyl; a phenyl group which may have one or more substitutents, for example, a lower alkyl group having 1 to 4 carbon atoms, such as methyl, ethyl, propyl, isopropyl, n-butyl, tert-butyl, isobutyl or sec-butyl, a lower alkoxy group having 1 to 4 carbon atoms, such as methoxy, ethoxy, propoxy or butoxy, a di(lower alkyl)amino group in which each alkyl has 1 to 3 carbon atoms, such as dimethylamino, diethylamino or dipropylamino, or a halogen atom such as fluorine, chlorine, bromine or iodine.

$R^4$, $R^5$, $R^6$, and $R^7$ may be the same or different and each is an alkyl group having 1 to 6 carbon atoms, an alicyclic group having 5 to 7 carbon atoms, a phenyl group which may have one or more substituents, an alkoxy group having 1 to 6 carbon atoms, a dialkylamino group in which each alkyl has 1 to 3 carbon atoms, a halogen atom, a benzyl group, a naphthyl group, or a halogen-substituted lower alkyl group having 1 or 2 carbon atoms, provided that $R^4$ and $R^5$ taken together and/or $R^6$ and $R^7$ taken together represent a fused benzene ring, a substituted fused benzene ring, a trimethylene group, a tetramethylene group, or a methylenedioxy group; and p, q, r, and s each is 0 to 5, provided that p+q and r+s each is in the range of from 0 to 5. Preferably, $R^4$, $R^5$, $R^6$, and $R^7$ may be the same or different and each is a lower alkyl group having 1 to 4 carbon atoms, a lower alkoxy group having 1 to 4 carbon atoms, a di(lower alkyl)amino group in which each alkyl has 1 or 2 carbon atoms, or a halogen atom, provided that $R^4$ and $R^5$ may and $R^6$ and $R^7$ may together represent a fused benzene ring or a methylenedioxy group. Furthermore, p, q, r, and s each preferably is 0 to 2.

Specific examples of $R^4$, $R^5$, $R^6$, and $R^7$ include a hydrogen atom; a lower alkyl group having 1 to 4 carbon atoms, such as methyl, ethyl, propyl, isopropyl, n-butyl, tert-butyl, isobutyl or sec-butyl; an alicyclic group having 5 to 7 carbon atoms, such as cyclopentyl, cyclohexyl or cycloheptyl; a phenyl group which may have one or more substitutents, for example, a lower alkyl group having 1 to 4 carbon atoms, such as methyl, ethyl, propyl, isopropyl, n-butyl, tert-butyl, isobutyl or sec-butyl, a lower alkoxy group having 1 to 4 carbon atoms, such as methoxy, ethoxy, propoxy or butoxy, a di(lower alkyl)amino group in which each alkyl has 1 to 3 carbon atoms, such as dimethylamino, diethylamino or dipropylamino, or a halogen atom such as fluorine, chlorine, bromine or iodine; a lower alkoxy group having 1 to 4 carbon atoms, such as methoxy, ethoxy, propoxy, or butoxy; a di(lower alkyl)amino group in which each alkyl has 1 to 3 carbon atoms, such as dimethylamino, diethylamino or dipropylamino; a halogen atom such as fluorine, chlorine, bromine or iodine; a benzyl group; a naphthyl group; or a halogen-substituted lower alkyl group having 1 or 2 carbon atoms, such as trifluoromethyl, trichloromethyl, or tribromomethyl.

Furthermore, $R^4$ and $R^5$ taken together and/or $R^6$ and $R^7$ taken together represent a fused benzene ring, a substituted fused benzene ring, a trimethylene group, a tetramethylene group, or a methylenedioxy group.

Preferred examples of the 2,2-(diaryl)vinylphosphine compound of the invention, which is represented by general formula (1) described above, include the compounds shown in Tables 1 to 17 given below. However, the compound of the invention should not be construed as being limited to these examples.

The abbreviations used in Tables 1 to 17 have the following meanings, respectively. The abbreviations used in compound names appearing hereinafter have the same meanings. The numeral preceding the abbreviation or symbol for a substituent indicates the position of the substituent on the phenyl group (for example, 4-Me means a methyl substituent bonded to the 4-position carbon atom of the phenyl group).

Me methyl
Et ethyl nPr n-propyl  
iPr isopropyl  
nBu n-butyl  
iBu isobutyl  
tBu tert-butyl  
MeO methoxy  
EtO ethoxy  
F fluorine atom  
Cl chlorine atom  
Br bromine atom  
Me$_2$N dimethylamino  
Et$_2$N diethylamino  
CyPe cyclopentyl  
CyHx cyclohexyl  
Ph phenyl  
p-Tol p-tolyl  
Xy 2,4-xylyl 2,3-benzene means that the substituents fuse with the benzene ring to form an α-naphthyl group.

3,4-benzene means that the substituents fuse with the benzene ring to form a β-naphthyl group.

TABLE 1

General Formula (1)

| Exemplified Compound | R$^1$ | R$^2$ | R$^3$ | p | R$^4$ | q | R$^5$ | r | R$^6$ | s | R$^7$ |
|---|---|---|---|---|---|---|---|---|---|---|---|
| 1  | H  | Me   | Me   | 0 | — | 0 | — | 0 | — | 0 | — |
| 2  | H  | Et   | Et   | 0 | — | 0 | — | 0 | — | 0 | — |
| 3  | H  | nPr  | nPr  | 0 | — | 0 | — | 0 | — | 0 | — |
| 4  | H  | iPr  | iPr  | 0 | — | 0 | — | 0 | — | 0 | — |
| 5  | H  | nBu  | nBu  | 0 | — | 0 | — | 0 | — | 0 | — |
| 6  | H  | iBu  | iBu  | 0 | — | 0 | — | 0 | — | 0 | — |
| 7  | H  | tBu  | tBu  | 0 | — | 0 | — | 0 | — | 0 | — |
| 8  | H  | CyPe | CyPe | 0 | — | 0 | — | 0 | — | 0 | — |
| 9  | H  | CyHx | CyHx | 0 | — | 0 | — | 0 | — | 0 | — |
| 10 | H  | Ph   | Ph   | 0 | — | 0 | — | 0 | — | 0 | — |
| 11 | Me | Me   | Me   | 0 | — | 0 | — | 0 | — | 0 | — |
| 12 | Me | Et   | Et   | 0 | — | 0 | — | 0 | — | 0 | — |
| 13 | Me | nPr  | nPr  | 0 | — | 0 | — | 0 | — | 0 | — |
| 14 | Me | iPr  | iPr  | 0 | — | 0 | — | 0 | — | 0 | — |
| 15 | Me | nBu  | nBu  | 0 | — | 0 | — | 0 | — | 0 | — |
| 16 | Me | iBu  | iBu  | 0 | — | 0 | — | 0 | — | 0 | — |
| 17 | Me | tBu  | tBu  | 0 | — | 0 | — | 0 | — | 0 | — |
| 18 | Me | CyPe | CyPe | 0 | — | 0 | — | 0 | — | 0 | — |
| 19 | Me | CyHx | CyHx | 0 | — | 0 | — | 0 | — | 0 | — |
| 20 | Me | Ph   | Ph   | 0 | — | 0 | — | 0 | — | 0 | — |

TABLE 2

General Formula (1)

| Exemplified Compound | R$^1$ | R$^2$ | R$^3$ | p | R$^4$ | q | R$^5$ | r | R$^6$ | s | R$^7$ |
|---|---|---|---|---|---|---|---|---|---|---|---|
| 21 | Et  | Me   | Me   | 0 | — | 0 | — | 0 | — | 0 | — |
| 22 | Et  | Et   | Et   | 0 | — | 0 | — | 0 | — | 0 | — |
| 23 | Et  | nPr  | nPr  | 0 | — | 0 | — | 0 | — | 0 | — |
| 24 | Et  | iPr  | iPr  | 0 | — | 0 | — | 0 | — | 0 | — |
| 25 | Et  | nBu  | nBu  | 0 | — | 0 | — | 0 | — | 0 | — |
| 26 | Et  | iBu  | iBu  | 0 | — | 0 | — | 0 | — | 0 | — |
| 27 | Et  | tBu  | tBu  | 0 | — | 0 | — | 0 | — | 0 | — |
| 28 | Et  | CyPe | CyPe | 0 | — | 0 | — | 0 | — | 0 | — |
| 29 | Et  | CyHx | CyHx | 0 | — | 0 | — | 0 | — | 0 | — |
| 30 | Et  | Ph   | Ph   | 0 | — | 0 | — | 0 | — | 0 | — |
| 31 | nPr | Me   | Me   | 0 | — | 0 | — | 0 | — | 0 | — |
| 32 | nPr | Et   | Et   | 0 | — | 0 | — | 0 | — | 0 | — |
| 33 | nPr | nPr  | nPr  | 0 | — | 0 | — | 0 | — | 0 | — |
| 34 | nPr | iPr  | iPr  | 0 | — | 0 | — | 0 | — | 0 | — |
| 35 | nPr | nBu  | nBu  | 0 | — | 0 | — | 0 | — | 0 | — |
| 36 | nPr | iBu  | iBu  | 0 | — | 0 | — | 0 | — | 0 | — |
| 37 | nPr | tBu  | tBu  | 0 | — | 0 | — | 0 | — | 0 | — |
| 38 | nPr | CyPe | CyPe | 0 | — | 0 | — | 0 | — | 0 | — |
| 39 | nPr | CyHx | CyHx | 0 | — | 0 | — | 0 | — | 0 | — |
| 40 | nPr | Ph   | Ph   | 0 | — | 0 | — | 0 | — | 0 | — |

TABLE 3

General Formula (1)

| Exemplified Compound | R$^1$ | R$^2$ | R$^3$ | p | R$^4$ | q | R$^5$ | r | R$^6$ | s | R$^7$ |
|---|---|---|---|---|---|---|---|---|---|---|---|
| 41 | iPr | Me   | Me   | 0 | — | 0 | — | 0 | — | 0 | — |
| 42 | iPr | Et   | Et   | 0 | — | 0 | — | 0 | — | 0 | — |
| 43 | iPr | nPr  | nPr  | 0 | — | 0 | — | 0 | — | 0 | — |
| 44 | iPr | iPr  | iPr  | 0 | — | 0 | — | 0 | — | 0 | — |
| 45 | iPr | nBu  | nBu  | 0 | — | 0 | — | 0 | — | 0 | — |
| 46 | iPr | iBu  | iBu  | 0 | — | 0 | — | 0 | — | 0 | — |
| 47 | iPr | tBu  | tBu  | 0 | — | 0 | — | 0 | — | 0 | — |
| 48 | iPr | CyPe | CyPe | 0 | — | 0 | — | 0 | — | 0 | — |
| 49 | iPr | CyHx | CyHx | 0 | — | 0 | — | 0 | — | 0 | — |
| 50 | iPr | Ph   | Ph   | 0 | — | 0 | — | 0 | — | 0 | — |
| 51 | nBu | Me   | Me   | 0 | — | 0 | — | 0 | — | 0 | — |
| 52 | nBu | Et   | Et   | 0 | — | 0 | — | 0 | — | 0 | — |
| 53 | nBu | nPr  | nPr  | 0 | — | 0 | — | 0 | — | 0 | — |
| 54 | nBu | iPr  | iPr  | 0 | — | 0 | — | 0 | — | 0 | — |
| 55 | nBu | nBu  | nBu  | 0 | — | 0 | — | 0 | — | 0 | — |
| 56 | nBu | iBu  | iBu  | 0 | — | 0 | — | 0 | — | 0 | — |
| 57 | nBu | tBu  | tBu  | 0 | — | 0 | — | 0 | — | 0 | — |
| 58 | nBu | CyPe | CyPe | 0 | — | 0 | — | 0 | — | 0 | — |
| 59 | nBu | CyHx | CyHx | 0 | — | 0 | — | 0 | — | 0 | — |
| 60 | nBu | Ph   | Ph   | 0 | — | 0 | — | 0 | — | 0 | — |

TABLE 4

General Formula (1)

| Exemplified Compound | R$^1$ | R$^2$ | R$^3$ | p | R$^4$ | q | R$^5$ | r | R$^6$ | s | R$^7$ |
|---|---|---|---|---|---|---|---|---|---|---|---|
| 61 | iBu | Me   | Me   | 0 | — | 0 | — | 0 | — | 0 | — |
| 62 | iBu | Et   | Et   | 0 | — | 0 | — | 0 | — | 0 | — |
| 63 | iBu | nPr  | nPr  | 0 | — | 0 | — | 0 | — | 0 | — |
| 64 | iBu | iPr  | iPr  | 0 | — | 0 | — | 0 | — | 0 | — |
| 65 | iBu | nBu  | nBu  | 0 | — | 0 | — | 0 | — | 0 | — |
| 66 | iBu | iBu  | iBu  | 0 | — | 0 | — | 0 | — | 0 | — |
| 67 | iBu | tBu  | tBu  | 0 | — | 0 | — | 0 | — | 0 | — |
| 68 | iBu | CyPe | CyPe | 0 | — | 0 | — | 0 | — | 0 | — |
| 69 | iBu | CyHx | CyHx | 0 | — | 0 | — | 0 | — | 0 | — |
| 70 | iBu | Ph   | Ph   | 0 | — | 0 | — | 0 | — | 0 | — |
| 71 | tBu | Me   | Me   | 0 | — | 0 | — | 0 | — | 0 | — |
| 72 | tBu | Et   | Et   | 0 | — | 0 | — | 0 | — | 0 | — |
| 73 | tBu | nPr  | nPr  | 0 | — | 0 | — | 0 | — | 0 | — |
| 74 | tBu | iPr  | iPr  | 0 | — | 0 | — | 0 | — | 0 | — |
| 75 | tBu | nBu  | nBu  | 0 | — | 0 | — | 0 | — | 0 | — |
| 76 | tBu | iBu  | iBu  | 0 | — | 0 | — | 0 | — | 0 | — |
| 77 | tBu | tBu  | tBu  | 0 | — | 0 | — | 0 | — | 0 | — |
| 78 | tBu | CyPe | CyPe | 0 | — | 0 | — | 0 | — | 0 | — |
| 79 | tBu | CyHx | CyHx | 0 | — | 0 | — | 0 | — | 0 | — |
| 80 | tBu | Ph   | Ph   | 0 | — | 0 | — | 0 | — | 0 | — |

TABLE 5

General Formula (1)

| Exemplified Compound | R¹ | R² | R³ | p | R⁴ | q | R⁵ | r | R⁶ | s | R⁷ |
|---|---|---|---|---|---|---|---|---|---|---|---|
| 81 | CyHx | Me | Me | 0 | — | 0 | — | 0 | — | 0 | — |
| 82 | CyHx | Et | Et | 0 | — | 0 | — | 0 | — | 0 | — |
| 83 | CyHx | nPr | nPr | 0 | — | 0 | — | 0 | — | 0 | — |
| 84 | CyHx | iPr | iPr | 0 | — | 0 | — | 0 | — | 0 | — |
| 85 | CyHx | nBu | nBu | 0 | — | 0 | — | 0 | — | 0 | — |
| 86 | CyHx | iBu | iBu | 0 | — | 0 | — | 0 | — | 0 | — |
| 87 | CyHx | tBu | tBu | 0 | — | 0 | — | 0 | — | 0 | — |
| 88 | CyHx | CyPe | CyPe | 0 | — | 0 | — | 0 | — | 0 | — |
| 89 | CyHx | CyHx | CyHx | 0 | — | 0 | — | 0 | — | 0 | — |
| 90 | CyHx | Ph | Ph | 0 | — | 0 | — | 0 | — | 0 | — |
| 91 | Ph | Me | Me | 0 | — | 0 | — | 0 | — | 0 | — |
| 92 | Ph | Et | Et | 0 | — | 0 | — | 0 | — | 0 | — |
| 93 | Ph | nPr | nPr | 0 | — | 0 | — | 0 | — | 0 | — |
| 94 | Ph | iPr | iPr | 0 | — | 0 | — | 0 | — | 0 | — |
| 95 | Ph | nBu | nBu | 0 | — | 0 | — | 0 | — | 0 | — |
| 96 | Ph | iBu | iBu | 0 | — | 0 | — | 0 | — | 0 | — |
| 97 | Ph | tBu | tBu | 0 | — | 0 | — | 0 | — | 0 | — |
| 98 | Ph | CyPe | CyPe | 0 | — | 0 | — | 0 | — | 0 | — |
| 99 | Ph | CyHx | CyHx | 0 | — | 0 | — | 0 | — | 0 | — |
| 100 | Ph | Ph | Ph | 0 | — | 0 | — | 0 | — | 0 | — |

TABLE 6

General Formula (1)

| Exemplified Compound | R¹ | R² | R³ | p | R⁴ | q | R⁵ | r | R⁶ | s | R⁷ |
|---|---|---|---|---|---|---|---|---|---|---|---|
| 101 | Me | Ph | Ph | 1 | 4-Me | 0 | — | 1 | 4-Me | 0 | — |
| 102 | Me | Ph | Ph | 1 | 4-Et | 0 | — | 1 | 4-Et | 0 | — |
| 103 | Me | Ph | Ph | 1 | 4-MeO | 0 | — | 1 | 4-MeO | 0 | — |
| 104 | Me | Ph | Ph | 1 | 4-EtO | 0 | — | 1 | 4-EtO | 0 | — |
| 105 | Me | Ph | Ph | 1 | 4-Me₂N | 0 | — | 1 | 4-Me₂N | 0 | — |
| 106 | Me | Ph | Ph | 1 | 4-Et₂N | 0 | — | 1 | 4-Et₂N | 0 | — |
| 107 | Me | Ph | Ph | 1 | 4-F | 0 | — | 1 | 4-F | 0 | — |
| 108 | Me | Ph | Ph | 1 | 4-Cl | 0 | — | 1 | 4-Cl | 0 | — |
| 109 | Me | Ph | Ph | 1 | 4-Br | 0 | — | 1 | 4-Br | 0 | — |
| 110 | Me | Ph | Ph | 1 | 3-Me | 1 | 5-Me | 1 | 3-Me | 1 | 5-Me |
| 111 | Me | Ph | Ph | | 3,4-OCH₂O— | | | | 3,4-OCH₂O— | | |
| 112 | Me | Ph | Ph | 5 | Me | 0 | — | 5 | Me | 0 | — |
| 113 | Me | Ph | Ph | 1 | 3-MeO | 1 | 4-MeO | 1 | 3-MeO | 1 | 4-MeO |
| 114 | Me | nPr | nPr | 1 | 4-Me₂N | 0 | — | 1 | 4-Me₂N | 0 | — |
| 115 | Me | iPr | iPr | 1 | 4-Me₂N | 0 | — | 1 | 4-Me₂N | 0 | — |
| 116 | Me | nBu | nBu | 1 | 4-Me₂N | 0 | — | 1 | 4-Me₂N | 0 | — |
| 117 | Me | iBu | iBu | 1 | 4-Me₂N | 0 | — | 1 | 4-Me₂N | 0 | — |
| 118 | Me | tBu | tBu | 1 | 4-Me₂N | 0 | — | 1 | 4-Me₂N | 0 | — |
| 119 | Me | CyPe | CyPe | 1 | 4-Me₂N | 0 | — | 1 | 4-Me₂N | 0 | — |
| 120 | Me | CyHx | CyHx | 1 | 4-Me₂N | 0 | — | 1 | 4-Me₂N | 0 | — |

TABLE 7

General Formula (1)

| Exemplified Compound | R¹ | R² | R³ | p | R⁴ | q | R⁵ | r | R⁶ | s | R⁷ |
|---|---|---|---|---|---|---|---|---|---|---|---|
| 121 | Ph | Ph | Ph | 1 | 4-Me | 0 | — | 1 | 4-Me | 0 | — |
| 122 | Ph | Ph | Ph | 1 | 4-Et | 0 | — | 1 | 4-Et | 0 | — |
| 123 | Ph | Ph | Ph | 1 | 4-MeO | 0 | — | 1 | 4-MeO | 0 | — |
| 124 | Ph | Ph | Ph | 1 | 4-EtO | 0 | — | 1 | 4-EtO | 0 | — |
| 125 | Ph | Ph | Ph | 1 | 4-Me₂N | 0 | — | 1 | 4-Me₂N | 0 | — |
| 126 | Ph | Ph | Ph | 1 | 4-Et₂N | 0 | — | 1 | 4-Et₂N | 0 | — |
| 127 | Ph | Ph | Ph | 1 | 4-F | 0 | — | 1 | 4-F | 0 | — |
| 128 | Ph | Ph | Ph | 1 | 4-Cl | 0 | — | 1 | 4-Cl | 0 | — |
| 129 | Ph | Ph | Ph | 1 | 4-Br | 0 | — | 1 | 4-Br | 0 | — |
| 130 | Ph | Ph | Ph | 1 | 3-Me | 1 | 5-Me | 1 | 3-Me | 1 | 5-Me |
| 131 | Ph | Ph | Ph | | 3,4-OCH₂O— | | | | 3,4-OCH₂O— | | |
| 132 | Ph | Ph | Ph | 5 | Me | 0 | — | 5 | Me | 0 | — |
| 133 | Ph | Ph | Ph | 1 | 3-MeO | 1 | 4-MeO | 1 | 3-MeO | 1 | 4-MeO |
| 134 | Ph | nPr | nPr | 1 | 4-Me₂N | 0 | — | 1 | 4-Me₂N | 0 | — |
| 135 | Ph | iPr | iPr | 1 | 4-Me₂N | 0 | — | 1 | 4-Me₂N | 0 | — |
| 136 | Ph | nBu | nBu | 1 | 4-Me₂N | 0 | — | 1 | 4-Me₂N | 0 | — |
| 137 | Ph | iBu | iBu | 1 | 4-Me₂N | 0 | — | 1 | 4-Me₂N | 0 | — |

TABLE 7-continued

General Formula (1)

| Exemplified Compound | $R^1$ | $R^2$ | $R^3$ | p | $R^4$ | q | $R^5$ | r | $R^6$ | s | $R^7$ |
|---|---|---|---|---|---|---|---|---|---|---|---|
| 138 | Ph | tBu | tBu | 1 | 4-Me$_2$N | 0 | — | 1 | 4-Me$_2$N | 0 | — |
| 139 | Ph | CyPe | CyPe | 1 | 4-Me$_2$N | 0 | — | 1 | 4-Me$_2$N | 0 | — |
| 140 | Ph | CyHx | CyHx | 1 | 4-Me$_2$N | 0 | — | 1 | 4-Me$_2$N | 0 | — |

TABLE 8

General Formula (1)

| Exemplified Compound | $R^1$ | $R^2$ | $R^3$ | p | $R^4$ | q | $R^5$ | r | $R^6$ | s | $R^7$ |
|---|---|---|---|---|---|---|---|---|---|---|---|
| 141 | Me | Ph | Ph | 1 | 4-Ph | 0 | — | 1 | 4-Ph | 0 | — |
| 142 | Me | Ph | Ph | 0 | — | 0 | — | 1 | 4-Me | 1 | 2-Me |
| 143 | Me | iPr | iPr | 1 | 4-Me | 0 | — | 0 | — | 0 | — |
| 144 | Me | iPr | iPr | 1 | 4-Me | 0 | — | 1 | 4-Me | 0 | — |
| 145 | Me | iPr | iPr | 1 | 4-tBu | 0 | — | 1 | 4-tBu | 0 | — |
| 146 | Me | iPr | iPr | 1 | 4-MeO | 0 | — | 1 | 4-MeO | 0 | — |
| 147 | Me | iPr | iPr | 1 | 2-Me | 1 | 4-Me | 1 | 2-Me | 1 | 4-Me |
| 148 | Me | iPr | iPr | 1 | 2-MeO | 1 | 4-MeO | 1 | 2-MeO | 1 | 4-MeO |
| 149 | Me | iPr | iPr | 1 | 4-Ph | 0 | — | 1 | 4-Ph | 0 | — |
| 150 | Me | CyHx | CyHx | 1 | 4-Me | 0 | — | 1 | 4-Me | 0 | — |
| 151 | Me | CyHx | CyHx | 1 | 4-MeO | 0 | — | 1 | 4-MeO | 0 | — |
| 152 | Me | CyHx | CyHx | 1 | 2-Me | 1 | 4-Me | 1 | 2-Me | 1 | 4-Me |
| 153 | Me | CyHx | CyHx | 1 | 2-MeO | 1 | 4-MeO | 1 | 2-MeO | 1 | 4-MeO |
| 154 | Me | CyHx | CyHx | 1 | 4-F | 0 | — | 1 | 4-F | 0 | — |
| 155 | Me | CyHx | CyHx | 1 | 4-tBu | 0 | — | 1 | 4-tBu | 0 | — |
| 156 | Me | CyHx | CyHx | 1 | 4-Cl | 0 | — | 1 | 4-Cl | 0 | — |
| 157 | Me | CyHx | CyHx | | 2,3-benzene | | | | 2,3-benzene | | |
| 158 | Me | CyHx | CyHx | | 3,4-benzene | | | | 3,4-benzene | | |
| 159 | Me | CyHx | CyHx | | 3,4-OCH$_2$O— | | | | 3,4-OCH$_2$O— | | |
| 160 | Me | CyHx | CyHx | | 2,3-(CH$_2$)$_4$— | | | | 2,3-(CH$_2$)$_4$— | | |

TABLE 9

General Formula (1)

| Exemplified Compound | $R^1$ | $R^2$ | $R^3$ | p | $R^4$ | q | $R^5$ | r | $R^6$ | s | $R^7$ |
|---|---|---|---|---|---|---|---|---|---|---|---|
| 161 | Me | CyHx | CyHx | | 2,3-(CH$_2$)$_3$— | | | | 2,3-(CH$_2$)$_3$— | | |
| 162 | Me | tBu | tBu | 1 | 4-Me | 0 | — | 0 | — | 0 | — |
| 163 | Me | tBu | tBu | 1 | 4-Me$_2$N | 1 | 2-Me | 1 | 4-Me$_2$N | 1 | 2-Me |
| 164 | Me | tBu | tBu | 1 | 4-MeO | 0 | — | 1 | 4-MeO | 0 | — |
| 165 | Me | tBu | tBu | 1 | 2-Me | 1 | 4-Me | 1 | 2-Me | 1 | 4-Me |
| 166 | Me | tBu | tBu | 1 | 2-MeO | 1 | 4-MeO | 1 | 2-MeO | 1 | 4-MeO |
| 167 | Me | tBu | tBu | 1 | 4-F | 0 | — | 1 | 4-F | 0 | — |
| 168 | Me | tBu | tBu | 1 | 4-tBu | 0 | — | 1 | 4-tBu | 0 | — |
| 169 | Me | tBu | tBu | 1 | 4-Cl | 0 | — | 1 | 4-Cl | 0 | — |
| 170 | Me | tBu | tBu | 1 | 4-Me$_2$N | 1 | 2-Me | 1 | 4-Me$_2$N | 1 | 2-Me |
| 171 | Me | tBu | tBu | | 2,3-benzene | | | | 2,3-benzene | | |
| 172 | Me | tBu | tBu | | 3,4-benzene | | | | 3,4-benzene | | |
| 173 | Me | tBu | tBu | | 3,4-OCH$_2$O— | | | | 3,4-OCH$_2$O— | | |
| 174 | Me | tBu | tBu | | 2,3-(CH$_2$)$_4$— | | | | 2,3-(CH$_2$)$_4$— | | |
| 175 | Me | tBu | tBu | | 2,3-(CH$_2$)$_3$— | | | | 2,3-(CH$_2$)$_3$— | | |
| 176 | Me | p-Tol | p-Tol | 0 | — | 0 | — | 0 | — | 0 | — |
| 177 | Me | p-Tol | p-Tol | 1 | 4-Me | 0 | — | 1 | 4-Me | 0 | — |
| 178 | Me | p-Tol | p-Tol | 1 | 4-Me$_2$N | 0 | — | 1 | 4-Me$_2$N | 0 | — |
| 179 | Me | Xy | Xy | 0 | — | 0 | — | 1 | — | 0 | — |
| 180 | Me | Xy | Xy | 1 | 4-Me$_2$N | 0 | — | 1 | 4-Me$_2$N | 0 | — |

TABLE 10

General Formula (1)

| Exemplified Compound | R¹ | R² | R³ | p | R⁴ | q | R⁵ | r | R⁶ | s | R⁷ |
|---|---|---|---|---|---|---|---|---|---|---|---|
| 181 | iPr | Ph | Ph | 1 | 4-Ph | 0 | — | 1 | 4-Ph | 0 | — |
| 182 | iPr | Ph | Ph | 0 | — | 0 | — | 1 | 4-Me | 1 | 2-Me |
| 183 | iPr | iPr | iPr | 1 | 4-Me | 0 | — | 0 | — | 0 | — |
| 184 | iPr | iPr | iPr | 1 | 4-Me | 0 | — | 1 | 4-Me | 0 | — |
| 185 | iPr | iPr | iPr | 1 | 4-tBu | 0 | — | 1 | 4-tBu | 0 | — |
| 186 | iPr | iPr | iPr | 1 | 4-MeO | 0 | — | 1 | 4-MeO | 0 | — |
| 187 | iPr | iPr | iPr | 1 | 2-Me | 1 | 4-Me | 1 | 2-Me | 1 | 4-Me |
| 188 | iPr | iPr | iPr | 1 | 2-MeO | 1 | 4-MeO | 1 | 2-MeO | 1 | 4-MeO |
| 189 | iPr | iPr | iPr | 1 | 4-Ph | 0 | — | 1 | 4-Ph | 0 | — |
| 190 | iPr | CyHx | CyHx | 1 | 4-Me | 0 | — | 1 | 4-Me | 0 | — |
| 191 | iPr | CyHx | CyHx | 1 | 4-MeO | 0 | — | 1 | 4-MeO | 0 | — |
| 192 | iPr | CyHx | CyHx | 1 | 2-Me | 1 | 4-Me | 1 | 2-Me | 1 | 4-Me |
| 193 | iPr | CyHx | CyHx | 1 | 2-MeO | 1 | 4-MeO | 1 | 2-MeO | 1 | 4-MeO |
| 194 | iPr | CyHx | CyHx | 1 | 4-F | 0 | — | 1 | 4-F | 0 | — |
| 195 | iPr | CyHx | CyHx | 1 | 4-tBu | 0 | — | 1 | 4-tBu | 0 | — |
| 196 | iPr | CyHx | CyHx | 1 | 4-Cl | 0 | — | 1 | 4-Cl | 0 | — |
| 197 | iPr | CyHx | CyHx | | 2,3-benzene | | | | 2,3-benzene | | |
| 198 | iPr | CyHx | CyHx | | 3,4-benzene | | | | 3,4-benzene | | |
| 199 | iPr | CyHx | CyHx | | 3,4-OCH₂O— | | | | 3,4-OCH₂O— | | |
| 200 | iPr | CyHx | CyHx | | 2,3-(CH₂)₄— | | | | 2,3-(CH₂)₄— | | |

TABLE 11

General Formula (1)

| Exemplified Compound | R¹ | R² | R³ | p | R⁴ | q | R⁵ | r | R⁶ | s | R⁷ |
|---|---|---|---|---|---|---|---|---|---|---|---|
| 201 | iPr | CyHx | CyHx | | 2,3-(CH₂)₃— | | | | 2,3-(CH₂)₃— | | |
| 202 | iPr | tBu | tBu | 1 | 4-Me | 0 | — | 0 | — | 0 | — |
| 203 | iPr | tBu | tBu | 1 | 4-Me₂N | 0 | — | 1 | 4-Me₂N | 0 | — |
| 204 | iPr | tBu | tBu | 1 | 4-MeO | 0 | — | 1 | 4-MeO | 0 | — |
| 205 | iPr | tBu | tBu | 1 | 2-Me | 1 | 4-Me | 1 | 2-Me | 1 | 4-Me |
| 206 | iPr | tBu | tBu | 1 | 2-MeO | 1 | 4-MeO | 1 | 2-MeO | 1 | 4-MeO |
| 207 | iPr | tBu | tBu | 1 | 4-F | 0 | — | 1 | 4-F | 0 | — |
| 208 | iPr | tBu | tBu | 1 | 4-tBu | 0 | — | 1 | 4-tBu | 0 | — |
| 209 | iPr | tBu | tBu | 1 | 4-Cl | 0 | — | 1 | 4-Cl | 0 | — |
| 210 | iPr | tBu | tBu | 1 | 4-Me₂N | 1 | 2-Me | 1 | 4-Me₂N | 1 | 2-Me |
| 211 | iPr | tBu | tBu | | 2,3-benzene | | | | 2,3-benzene | | |
| 212 | iPr | tBu | tBu | | 3,4-benzene | | | | 3,4-benzene | | |
| 213 | iPr | tBu | tBu | | 3,4-OCH₂O— | | | | 3,4-OCH₂O— | | |
| 214 | iPr | tBu | tBu | | 2,3-(CH₂)₄— | | | | 2,3-(CH₂)₄— | | |
| 215 | iPr | tBu | tBu | | 2,3-(CH₂)₃— | | | | 2,3-(CH₂)₃— | | |
| 216 | iPr | p-Tol | p-Tol | 0 | — | 0 | — | 0 | — | 0 | — |
| 217 | iPr | p-Tol | p-Tol | 1 | 4-Me | 0 | — | 1 | 4-Me | 0 | — |
| 218 | iPr | p-Tol | p-Tol | 1 | 4-Me₂N | 0 | — | 1 | 4-Me₂N | 0 | — |
| 219 | iPr | Xy | Xy | 0 | — | 0 | — | 1 | — | 0 | — |
| 220 | iPr | Xy | Xy | 1 | 4-Me₂N | 0 | — | 1 | 4-Me₂N | 0 | — |

TABLE 12

General Formula (1)

| Exemplified Compound | R¹ | R² | R³ | p | R⁴ | q | R⁵ | r | R⁶ | s | R⁷ |
|---|---|---|---|---|---|---|---|---|---|---|---|
| 221 | CyHx | Ph | Ph | 1 | 4-Ph | 0 | — | 1 | 4-Ph | 0 | — |
| 222 | CyHx | Ph | Ph | 0 | — | 0 | — | 1 | 4-Me | 1 | 2-Me |
| 223 | CyHx | iPr | iPr | 1 | 4-Me | 0 | — | 0 | — | 0 | — |
| 224 | CyHx | iPr | iPr | 1 | 4-Me | 0 | — | 1 | 4-Me | 0 | — |
| 225 | CyHx | iPr | iPr | 1 | 4-tBu | 0 | — | 1 | 4-tBu | 0 | — |
| 226 | CyHx | iPr | iPr | 1 | 4-MeO | 0 | — | 1 | 4-MeO | 0 | — |
| 227 | CyHx | iPr | iPr | 1 | 2-Me | 1 | 4-Me | 1 | 2-Me | 1 | 4-Me |
| 228 | CyHx | iPr | iPr | 1 | 2-MeO | 1 | 4-MeO | 1 | 2-MeO | 1 | 4-MeO |
| 229 | CyHx | iPr | iPr | 1 | 4-Ph | 0 | — | 1 | 4-Ph | 0 | — |
| 230 | CyHx | CyHx | CyHx | 1 | 4-Me | 0 | — | 1 | 4-Me | 0 | — |
| 231 | CyHx | CyHx | CyHx | 1 | 4-MeO | 0 | — | 1 | 4-MeO | 0 | — |
| 232 | CyHx | CyHx | CyHx | 1 | 2-Me | 1 | 4-Me | 1 | 2-Me | 1 | 4-Me |
| 233 | CyHx | CyHx | CyHx | 1 | 2-MeO | 1 | 4-MeO | 1 | 2-MeO | 1 | 4-MeO |

TABLE 12-continued

General Formula (1)

| Exemplified Compound | $R^1$ | $R^2$ | $R^3$ | p | $R^4$ | q | $R^5$ | r | $R^6$ | s | $R^7$ |
|---|---|---|---|---|---|---|---|---|---|---|---|
| 234 | CyHx | CyHx | CyHx | 1 | 4-F | 0 | — | 1 | 4-F | 0 | — |
| 235 | CyHx | CyHx | CyHx | 1 | 4-tBu | 0 | — | 1 | 4-tBu | 0 | — |
| 236 | CyHx | CyHx | CyHx | 1 | 4-Cl | 0 | — | 1 | 4-Cl | 0 | — |
| 237 | CyHx | CyHx | CyHx | | 2,3-benzene | | | | 2,3-benzene | | |
| 238 | CyHx | CyHx | CyHx | | 3,4-benzene | | | | 3,4-benzene | | |
| 239 | CyHx | CyHx | CyHx | | 3,4-OCH$_2$O— | | | | 3,4-OCH$_2$O— | | |
| 240 | CyHx | CyHx | CyHx | | 2,3-(CH$_2$)$_4$— | | | | 2,3-(CH$_2$)$_4$— | | |

TABLE 13

General Formula (1)

| Exemplified Compound | $R^1$ | $R^2$ | $R^3$ | p | $R^4$ | q | $R^5$ | r | $R^6$ | s | $R^7$ |
|---|---|---|---|---|---|---|---|---|---|---|---|
| 241 | CyHx | CyHx | CyHx | | 2,3-(CH$_2$)$_3$— | | | | 2,3-(CH$_2$)$_3$— | | |
| 242 | CyHx | tBu | tBu | 1 | 4-Me | 0 | — | 0 | — | 0 | — |
| 243 | CyHx | tBu | tBu | 1 | 4-Me$_2$N | 0 | — | 1 | 4-Me$_2$N | 0 | — |
| 244 | CyHx | tBu | tBu | 1 | 4-MeO | 0 | — | 1 | 4-MeO | 0 | — |
| 245 | CyHx | tBu | tBu | 1 | 2-Me | 1 | 4-Me | 1 | 2-Me | 1 | 4-Me |
| 246 | CyHx | tBu | tBu | 1 | 2-MeO | 1 | 4-MeO | 1 | 2-MeO | 1 | 4-MeO |
| 247 | CyHx | tBu | tBu | 1 | 4-F | 0 | — | 1 | 4-F | 0 | — |
| 248 | CyHx | tBu | tBu | 1 | 4-tBu | 0 | — | 1 | 4-tBu | 0 | — |
| 249 | CyHx | tBu | tBu | 1 | 4-Cl | 0 | — | 1 | 4-Cl | 0 | — |
| 250 | CyHx | tBu | tBu | 1 | 4-Me$_2$N | 1 | 2-Me | 1 | 4-Me$_2$N | 1 | 2-Me |
| 251 | CyHx | tBu | tBu | | 2,3-benzene | | | | 2,3-benzene | | |
| 252 | CyHx | tBu | tBu | | 3,4-benzene | | | | 3,4-benzene | | |
| 253 | CyHx | tBu | tBu | | 3,4-OCH$_2$O— | | | | 3,4-OCH$_2$O— | | |
| 254 | CyHx | tBu | tBu | | 2,3-(CH$_2$)$_4$— | | | | 2,3-(CH$_2$)$_4$— | | |
| 255 | CyHx | tBu | tBu | | 2,3-(CH$_2$)$_3$— | | | | 2,3-(CH$_2$)$_3$— | | |
| 256 | CyHx | p-Tol | p-Tol | 0 | — | 0 | — | 0 | — | 0 | — |
| 257 | CyHx | p-Tol | p-Tol | 1 | 4-Me | 0 | — | 1 | 4-Me | 0 | — |
| 258 | CyHx | p-Tol | p-Tol | 1 | 4-Me$_2$N | 0 | — | 1 | 4-Me$_2$N | 0 | — |
| 259 | CyHx | Xy | Xy | 0 | — | 0 | — | 1 | — | 0 | — |
| 260 | CyHx | Xy | Xy | 1 | 4-Me$_2$N | 0 | — | 1 | 4-Me$_2$N | 0 | — |

TABLE 14

General Formula (1)

| Exemplified Compound | $R^1$ | $R^2$ | $R^3$ | p | $R^4$ | q | $R^5$ | r | $R^6$ | s | $R^7$ |
|---|---|---|---|---|---|---|---|---|---|---|---|
| 261 | tBu | Ph | Ph | 1 | 4-Ph | 0 | — | 1 | 4-Ph | 0 | — |
| 262 | tBu | Ph | Ph | 0 | — | 0 | — | 1 | 4-Me | 1 | 2-Me |
| 263 | tBu | iPr | iPr | 1 | 4-Me | 0 | — | 0 | — | 0 | — |
| 264 | tBu | iPr | iPr | 1 | 4-Me | 0 | — | 1 | 4-Me | 0 | — |
| 265 | tBu | iPr | iPr | 1 | 4-tBu | 0 | — | 1 | 4-tBu | 0 | — |
| 266 | tBu | iPr | iPr | 1 | 4-MeO | 0 | — | 1 | 4-MeO | 0 | — |
| 267 | tBu | iPr | iPr | 1 | 2-Me | 1 | 4-Me | 1 | 2-Me | 1 | 4-Me |
| 268 | tBu | iPr | iPr | 1 | 2-MeO | 1 | 4-MeO | 1 | 2-MeO | 1 | 4-MeO |
| 269 | tBu | iPr | iPr | 1 | 4-Ph | 0 | — | 1 | 4-Ph | 0 | — |
| 270 | tBu | CyHx | CyHx | 1 | 4-Me | 0 | — | 1 | 4-Me | 0 | — |
| 271 | tBu | CyHx | CyHx | 1 | 4-MeO | 0 | — | 1 | 4-MeO | 0 | — |
| 272 | tBu | CyHx | CyHx | 1 | 2-Me | 1 | 4-Me | 1 | 2-Me | 1 | 4-Me |
| 273 | tBu | CyHx | CyHx | 1 | 2-MeO | 1 | 4-MeO | 1 | 2-MeO | 1 | 4-MeO |
| 274 | tBu | CyHx | CyHx | 1 | 4-F | 0 | — | 1 | 4-F | 0 | — |
| 275 | tBu | CyHx | CyHx | 1 | 4-tBu | 0 | — | 1 | 4-tBu | 0 | — |
| 276 | tBu | CyHx | CyHx | 1 | 4-Cl | 0 | — | 1 | 4-Cl | 0 | — |
| 277 | tBu | CyHx | CyHx | | 2,3-benzene | | | | 2,3-benzene | | |
| 278 | tBu | CyHx | CyHx | | 3,4-benzene | | | | 3,4-benzene | | |
| 279 | tBu | CyHx | CyHx | | 3,4-OCH$_2$O— | | | | 3,4-OCH$_2$O— | | |
| 280 | tBu | CyHx | CyHx | | 2,3-(CH$_2$)$_4$— | | | | 2,3-(CH$_2$)$_4$— | | |

TABLE 15

General Formula (1)

| Exemplified Compound | R¹ | R² | R³ | p | R⁴ | q | R⁵ | r | R⁶ | s | R⁷ |
|---|---|---|---|---|---|---|---|---|---|---|---|
| 281 | tBu | CyHx | CyHx |   | 2,3-(CH$_2$)$_3$— |   |   |   | 2,3-(CH$_2$)$_3$— |   |   |
| 282 | tBu | tBu | tBu | 1 | 4-Me | 0 | — | 0 | — | 0 | — |
| 283 | tBu | tBu | tBu | 1 | 4-Me$_2$N | 0 | — | 1 | 4-Me$_2$N | 0 | — |
| 284 | tBu | tBu | tBu | 1 | 4-MeO | 0 | — | 1 | 4-MeO | 0 | — |
| 285 | tBu | tBu | tBu | 1 | 2-Me | 1 | 4-Me | 1 | 2-Me | 1 | 4-Me |
| 286 | tBu | tBu | tBu | 1 | 2-MeO | 1 | 4-MeO | 1 | 2-MeO | 1 | 4-MeO |
| 287 | tBu | tBu | tBu | 1 | 4-F | 0 | — | 1 | 4-F | 0 | — |
| 288 | tBu | tBu | tBu | 1 | 4-tBu | 0 | — | 1 | 4-tBu | 0 | — |
| 289 | tBu | tBu | tBu | 1 | 4-Cl | 0 | — | 1 | 4-Cl | 0 | — |
| 290 | tBu | tBu | tBu | 1 | 4-Me$_2$N | 1 | 2-Me | 1 | 4-Me$_2$N | 1 | 2-Me |
| 291 | tBu | tBu | tBu |   | 2,3-benzene |   |   |   | 2,3-benzene |   |   |
| 292 | tBu | tBu | tBu |   | 3,4-benzene |   |   |   | 3,4-benzene |   |   |
| 293 | tBu | tBu | tBu |   | 3,4-OCH$_2$O— |   |   |   | 3,4-OCH$_2$O— |   |   |
| 294 | tBu | tBu | tBu |   | 2,3-(CH$_2$)$_4$— |   |   |   | 2,3-(CH$_2$)$_4$— |   |   |
| 295 | tBu | tBu | tBu |   | 2,3-(CH$_2$)$_3$— |   |   |   | 2,3-(CH$_2$)$_3$— |   |   |
| 296 | tBu | p-Tol | p-Tol | 0 | — | 0 | — | 0 | — | 0 | — |
| 297 | tBu | p-Tol | p-Tol | 1 | 4-Me | 0 | — | 1 | 4-Me | 0 | — |
| 298 | tBu | p-Tol | p-Tol | 1 | 4-Me$_2$N | 0 | — | 1 | 4-Me$_2$N | 0 | — |
| 299 | tBu | Xy | Xy | 0 | — | 0 | — | 1 | — | 0 | — |
| 300 | tBu | Xy | Xy | 1 | 4-Me$_2$N | 0 | — | 1 | 4-Me$_2$N | 0 | — |

TABLE 16

General Formula (1)

| Exemplified Compound | R¹ | R² | R³ | p | R⁴ | q | R⁵ | r | R⁶ | s | R⁷ |
|---|---|---|---|---|---|---|---|---|---|---|---|
| 301 | Ph | Ph | Ph | 1 | 4-Ph | 0 | — | 1 | 4-Ph | 0 | — |
| 302 | Ph | Ph | Ph | 0 | — | 0 | — | 1 | 4-Me | 1 | 2-Me |
| 303 | Ph | iPr | iPr | 1 | 4-Me | 0 | — | 0 | — | 0 | — |
| 304 | Ph | iPr | iPr | 1 | 4-Me | 0 | — | 1 | 4-Me | 0 | — |
| 305 | Ph | iPr | iPr | 1 | 4-tBu | 0 | — | 1 | 4-tBu | 0 | — |
| 306 | Ph | iPr | iPr | 1 | 4-MeO | 0 | — | 1 | 4-MeO | 0 | — |
| 307 | Ph | iPr | iPr | 1 | 2-Me | 1 | 4-Me | 1 | 2-Me | 1 | 4-Me |
| 308 | Ph | iPr | iPr | 1 | 2-MeO | 1 | 4-MeO | 1 | 2-MeO | 1 | 4-MeO |
| 309 | Ph | iPr | iPr | 1 | 4-Ph | 0 | — | 1 | 4-Ph | 0 | — |
| 310 | Ph | CyHx | CyHx | 1 | 4-Me | 0 | — | 1 | 4-Me | 0 | — |
| 311 | Ph | CyHx | CyHx | 1 | 4-MeO | 0 | — | 1 | 4-MeO | 0 | — |
| 312 | Ph | CyHx | CyHx | 1 | 2-Me | 1 | 4-Me | 1 | 2-Me | 1 | 4-Me |
| 313 | Ph | CyHx | CyHx | 1 | 2-MeO | 1 | 4-MeO | 1 | 2-MeO | 1 | 4-MeO |
| 314 | Ph | CyHx | CyHx | 1 | 4-F | 0 | — | 1 | 4-F | 0 | — |
| 315 | Ph | CyHx | CyHx | 1 | 4-tBu | 0 | — | 1 | 4-tBu | 0 | — |
| 316 | Ph | CyHx | CyHx | 1 | 4-Cl | 0 | — | 1 | 4-Cl | 0 | — |
| 317 | Ph | CyHx | CyHx |   | 2,3-benzene |   |   |   | 2,3-benzene |   |   |
| 318 | Ph | CyHx | CyHx |   | 3,4-benzene |   |   |   | 3,4-benzene |   |   |
| 319 | Ph | CyHx | CyHx |   | 3,4-OCH$_2$O— |   |   |   | 3,4-OCH$_2$O— |   |   |
| 320 | Ph | CyHx | CyHx |   | 2,3-(CH$_2$)$_4$— |   |   |   | 2,3-(CH$_2$)$_4$— |   |   |

TABLE 17

General Formula (1)

| Exemplified Compound | R¹ | R² | R³ | p | R⁴ | q | R⁵ | r | R⁶ | s | R⁷ |
|---|---|---|---|---|---|---|---|---|---|---|---|
| 321 | Ph | CyHx | CyHx |   | 2,3-(CH$_2$)$_3$— |   |   |   | 2,3-(CH$_2$)$_3$— |   |   |
| 322 | Ph | tBu | tBu | 1 | 4-Me | 0 | — | 0 | — | 0 | — |
| 323 | Ph | tBu | tBu | 1 | 4-Me$_2$N | 0 | — | 1 | 4-Me$_2$N | 0 | — |
| 324 | Ph | tBu | tBu | 1 | 4-MeO | 0 | — | 1 | 4-MeO | 0 | — |
| 325 | Ph | tBu | tBu | 1 | 2-Me | 1 | 4-Me | 1 | 2-Me | 1 | 4-Me |
| 326 | Ph | tBu | tBu | 1 | 2-MeO | 1 | 4-MeO | 1 | 2-MeO | 1 | 4-MeO |
| 327 | Ph | tBu | tBu | 1 | 4-F | 0 | — | 1 | 4-F | 0 | — |
| 328 | Ph | tBu | tBu | 1 | 4-tBu | 0 | — | 1 | 4-tBu | 0 | — |
| 329 | Ph | tBu | tBu | 1 | 4-Cl | 0 | — | 1 | 4-Cl | 0 | — |
| 330 | Ph | tBu | tBu | 1 | 4-Me$_2$N | 1 | 2-Me | 1 | 4-Me$_2$N | 1 | 2-Me |
| 331 | Ph | tBu | tBu |   | 2,3-benzene |   |   |   | 2,3-benzene |   |   |
| 332 | Ph | tBu | tBu |   | 3,4-benzene |   |   |   | 3,4-benzene |   |   |
| 333 | Ph | tBu | tBu |   | 3,4-OCH$_2$O— |   |   |   | 3,4-OCH$_2$O— |   |   |

TABLE 17-continued

General Formula (1)

| Exemplified Compound | $R^1$ | $R^2$ | $R^3$ | p | $R^4$ | q | $R^5$ | r | $R^6$ | s | $R^7$ |
|---|---|---|---|---|---|---|---|---|---|---|---|
| 334 | Ph | tBu | tBu | | 2,3-$(CH_2)_4$— | | | | 2,3-$(CH_2)_4$— | | |
| 335 | Ph | tBu | tBu | | 2,3-$(CH_2)_3$— | | | | 2,3-$(CH_2)_3$— | | |
| 336 | Ph | p-Tol | p-Tol | 0 | — | 0 | — | 0 | — | 0 | — |
| 337 | Ph | p-Tol | p-Tol | 1 | 4-Me | 0 | — | 1 | 4-Me | 0 | — |
| 338 | Ph | p-Tol | p-Tol | 1 | 4-$Me_2$N | 0 | — | 1 | 4-$Me_2$N | 0 | — |
| 339 | Ph | Xy | Xy | 0 | — | 0 | — | 1 | — | 0 | — |
| 340 | Ph | Xy | Xy | 1 | 4-$Me_2$N | 0 | — | 1 | 4-$Me_2$N | 0 | — |

The compound (1) of the invention is produced, for example, by the process shown by the following reaction formula.

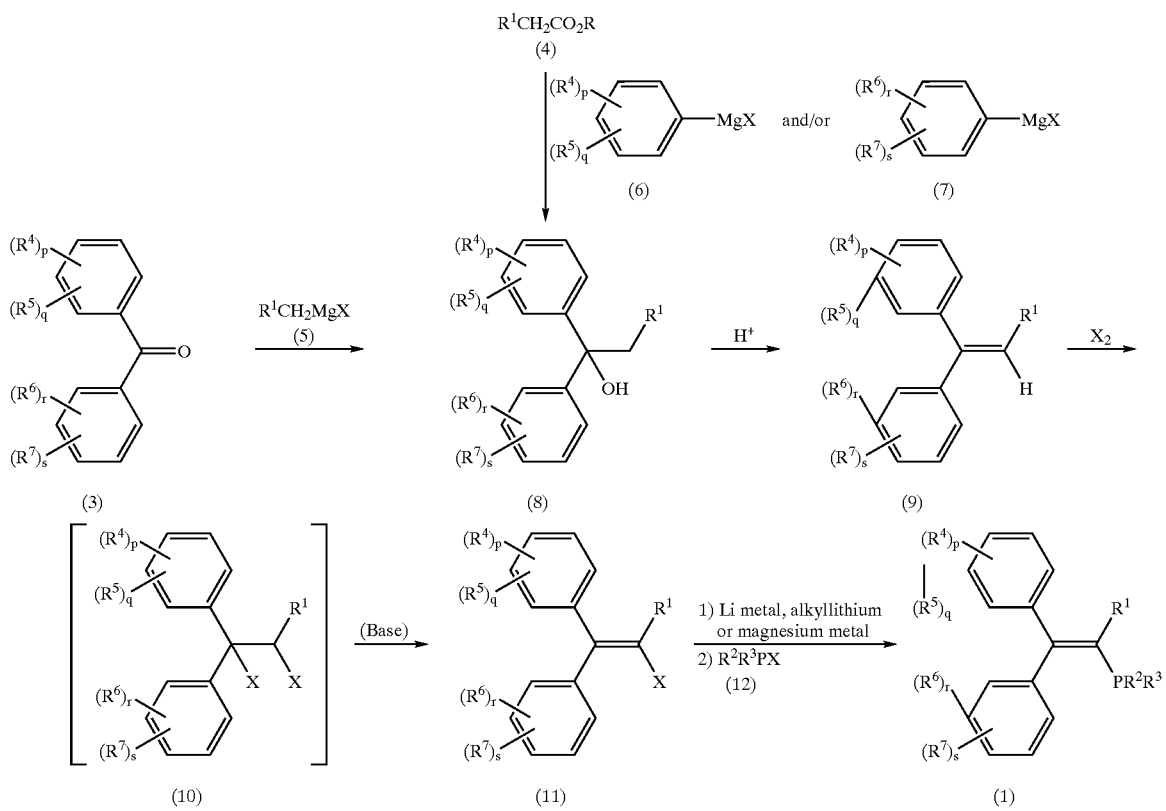

(In the formula, $R^1$, $R^2$, $R^3$, $R^4$, $R^5$, $R^6$, $R^7$, p, q, r, and s have the same meanings as defined above; X is a halogen atom; and R is a lower alkyl group having 1 to 4 carbon atoms.)

Specifically, the process comprises the following five steps as shown above.

First Step: A step in which an alcohol compound (8) is obtained by a) a method comprising the reaction of a diaryl ketone (3) with a Grignard reagent (5), or by b) a method comprising the reaction of an ester (4) with a Grignard reagent (6) and/or another Grignard reagent.

Second Step: A step in which the alcohol compound (8) is dehydrated with an acid catalyst (e.g., p-toluenesulfonic acid) to obtain a vinyl compound (9).

Third Step: A step in which the vinyl compound (9) is caused to addition reaction of a halogen to thereby obtain a dihalide compound (10).

Fourth Step: A step in which the dihalide compound (10) is subjected to dehydrohalogenation optionally in the presence of a base (e.g., pyridine) to obtain a vinyl halide compound (11).

Fifth Step: A step in which lithium metal, an alkyllithium, or magnesium metal is caused to act on the vinyl halide compound (11) to prepare a vinyllithium compound or vinyl Grignard reagent and this reaction product is subjected to coupling reaction with a phosphorus halide compound (12) to obtain a 2,2-(diaryl)vinylphosphine compound (1) of the invention.

In the compound (3) to compound (10) in the formula shown above, $R^1$, $R^2$, $R^3$, $R^4$, $R^5$, $R^6$, $R^7$, p, q, r, and s have the same meanings as defined above; X is a halogen atom; and R in the compound (4) is a lower alkyl group having 1 to 4 carbon atoms.

Examples of $R^1$, $R^2$, $R^3$, $R^4$, $R^5$, $R^6$, and $R^7$ include the same groups and atoms as enumerated above.

Examples of X include a halogen atom such as fluorine, chlorine, bromine or iodine.

Examples of R include a lower alkyl group having 1 to 4 carbon atoms such as methyl, ethyl, propyl, isopropyl, n-butyl, tert-butyl, isobutyl or sec-butyl.

As the diaryl ketone (3) and the ester (4) may be used a commercial diaryl ketone compound and a commercial ester compound (e.g., ones manufactured by Tokyo Kasei Kogyo Co., Ltd. and Nacalai Tesque, Inc.) without any treatment. Alternatively, the ketone (3) and ester (4) may be synthesized by known methods.

The Grignard reagents (5), (6), and (7) may be ones prepared by a known method from corresponding halogen compounds on the market or from halogen compounds synthesized by a known method.

For conducting the first step, in which an alcohol compound (8) is obtained by a) a method comprising the reaction of a diaryl ketone (3) with a Grignard reagent (5), or by b) a method comprising the raction of an ester (4) with a Grignard reagent (6) and/or another Grignard reagent, an ordinary Grignard reaction can be used.

In the Grignard reaction by method a), an alcohol compound (8) can be obtained by the reaction of a diaryl ketone (3) with a Grignard reagent (5).

The amount of the Grignard reagent (5) to be used is preferably about from 0.5 to 10 mol, more preferably about from 0.8 to 3.0 mol, per mol of the diaryl ketone (3).

Examples of reaction solvents include ether solvents such as diethyl ether, diisopropyl ether, tetrahydrofuran, dimethoxyethane, dioxane, and 1,3-dioxolane. Preferred of these are diethyl ether and tetrahydrofuran. Such a solvent may be used in an amount of preferably about from 1.0 to 80 times by volume, more preferably about from 2.0 to 30 times by volume, the amount of the diaryl ketone (3).

Appropriate additives may be added in conducting in this reaction in order to accelerate the reaction. Examples of the additives include cesium trichloride, zinc chloride, zinc bromide, copper chloride, copper bromide, copper iodide, aluminum trichloride, and titanium tetrachloride. Preferred of these are cesium trichloride, copper chloride, copper bromide, and copper iodide. The amount of such additives to be used is preferably about from 0.01 to 10 mol, more preferably about from 0.05 to 3.0 mol, per mol of the diaryl ketone (3).

This reaction is usually conducted under an inert gas atmosphere such as nitrogen gas or argon gas. In this reaction, the reaction time is generally about from 10 minutes to 30 hours, preferably about from 30 minutes to 12 hours, and the reaction temperature is generally about from −20 to 100° C., preferably about from 0 to 70° C. Although such conditions can be used to carry out the reaction, they may be suitably varied according to the kinds and amounts of the diaryl ketone (3) and Grignard reagent (5) to be used, etc.

In the Grignard reaction by method b), an alcohol compound (8) can be obtained by the reaction of an ester (4) with a Grignard reagent (6) and/or another Grignard reagent.

The amount of the Grignard reagents (6) and (7) to be used is preferably about from 1.0 to 10 mol, more preferably about from 1.6 to 4.8 mol, per mol of the ester (4).

Examples of reaction solvents include ether solvents such as diethyl ether, diisopropyl ether, tetrahydrofuran, dimethoxyethane, dioxane, and 1,3-dioxolane. Preferred of these are diethyl ether and tetrahydrofuran. Such a solvent may be used in an amount of preferably about from 1.0 to 50 times by volume, more preferably about from 4.0 to 10 times by volume, the amount of the ester (4).

Appropriate additives may be added in conducting the reaction in order to accelerate the reaction. Examples of the additives include cesium trichloride, zinc chloride, zinc bromide, copper chloride, copper bromide, copper iodide, aluminum trichloride, and titanium tetrachloride. Preferred of these are cesium trichloride, copper chloride, copper bromide, and copper iodide. The amount of such additives to be used is preferably about from 0.01 to 10 mol, more preferably about from 0.05 to 3.0 mol, per mol of the ester (4).

This reaction is usually conducted under an inert gas atmosphere such as nitrogen gas or argon gas. In this reaction, the reaction time is generally about from 10 minutes to 30 hours, preferably about from 30 minutes to 8 hours, and the reaction temperature is generally about from −20 to 100° C., preferably about from 0 to 70° C. Although such conditions can be used to carry out the reaction, they may be suitably varied according to the kinds and amounts of the ester (4) and Grignard reagents (6) and (7) to be used, etc.

In each of a) and b) described above, an ordinary post-treatment is conducted after completion of the reaction, whereby the target compound can be obtained.

For conducting the second step, in which the alcohol compound (8) is dehydrated with an acid catalyst (e.g., p-toluenesulfonic acid) to obtain a vinyl compound (9), an ordinary dehydration reaction can be used.

Examples of the acid catalyst include hydrochloric acid, sulfuric acid, camphorsulfonic acid, benzenesulfonic acid, and p-toluenesulfonic acid. Preferred of these is p-toluenesulfonic acid. The amount of the acid catalyst to be used is preferably about from 0.0001 to 0.2 mol, more preferably about from 0.005 to 0.05 mol, per mol of the alcohol compound (8).

Examples of reaction solvents include aromatic hydrocarbons such as benzene, toluene, xylene, and chlorobenzene; and ether solvents such as diethyl ether, diisopropyl ether, tetrahydrofuran, dimethoxyethane, dioxane, and 1,3-dioxolane. Preferred of these are benzene, toluene, and xylene. Such a solvent may be used in an amount of preferably about from 1.0 to 50 times by volume, more preferably about from 2.0 to 20 times by volume, the amount of the alcohol compound (8).

This reaction is usually conducted under an inert gas atmosphere such as nitrogen gas or argon gas. In this reaction, the reaction time is generally about from 10 minutes to 30 hours, preferably about from 30 minutes to 8 hours, and the reaction temperature is generally about from 20 to 180° C., preferably about from 70 to 140° C. Although such conditions can be used to carry out the reaction, they may be suitably varied according to the kinds and amounts of the alcohol compound (8) and acid catalyst to be used, etc.

After completion of the reaction, an ordinary post-treatment is conducted, whereby the target compound can be obtained.

For conducting the third step, in which the vinyl compound (9) is caused to add a halogen to thereby obtain a dihalide compound (10), the ordinary halogen addition reaction to an olefin can be used.

Examples of the halogen include chlorine, bromine, and iodine, and bromine is preferred. The amount of the halogen to be used is preferably about from 0.5 to 2.0 mol, more preferably about from 0.8 to 1.2 mol, per mol of the vinyl compound (9).

Examples of reaction solvents include aromatic hydrocarbons such as benzene, toluene, xylene, and chlorobenzene;

ether solvents such as diethyl ether, diisopropyl ether, tetrahydrofuran, dimethoxyethane, dioxane, and 1,3-dioxolane; and halogenated solvents such as dichloromethane, chloroform, carbon tetrachloride, dichloroethane, dibromomethane, and dibromoethane. Preferred of these are halogenated solvents such as dichloromethane, dichloroethane, chloroform, and carbon tetrachloride. Such a solvent may be used in an amount of preferably about from 0.2 to 50 times by volume, more preferably about from 0.5 to 20 times by volume, the amount of the vinyl compound (9).

This reaction is usually conducted under an inert gas atmosphere such as nitrogen gas or argon gas. In this reaction, the reaction time is generally about from 10 minutes to 24 hours, preferably about from 30 minutes to 8 hours, and the reaction temperature is generally about from −60 to 100° C., preferably about from −30 to 50° C. Although such conditions can be used to carry out the reaction, they may be suitably varied according to the kinds and amounts of the vinyl compound (9) and halogen to be used, etc.

After completion of the reaction, an ordinary post-treatment is conducted, whereby the target compound can be obtained.

For conducting the fourth step, in which the dihalide compound (10) is subjected to dehydrohalogenation optionally in the presence of a base to obtain a vinyl halide compound (11), an ordinary dehydrohalogenation reaction can be used.

Examples of the base include triethylamine, dimethylaniline, diethylaniline, pyridine, picoline, lutidine, ethylpyridine, quinoline, and isoquinoline. Preferred of these is pyridine. Such a base may be used in an amount of preferably about from 0.5 to 30 mol, more preferably about from 1.0 to 10 mol, per mol of the dihalide compound (10).

Examples of reaction solvents include aromatic hydrocarbons such as benzene, toluene, xylene, and chlorobenzene; and ether solvents such as diethyl ether, diisopropyl ether, tetrahydrofuran, dimethoxyethane, dioxane, and 1,3-dioxolane. Preferred of these are benzene, toluene, and xylene. Such a solvent may be used in an amount of preferably about from 0.2 to 30 times by volume, more preferably about from 0.5 to 10 times by volume, the amount of the dihalide compound (10).

This reaction is usually conducted under an inert gas atmosphere such as nitrogen gas or argon gas. In this reaction, the reaction time is generally about from 10 minutes to 30 hours, preferably about from 30 minutes to 16 hours, and the reaction temperature is generally about from 20 to 140° C., preferably about from 60 to 110° C. Although such conditions can be used to carry out the reaction, they may be suitably varied according to the kinds and amounts of the dihalide compound (10) and base to be used, etc.

After completion of the reaction, an ordinary post-treatment is conducted, whereby the target compound can be obtained.

For conducting the fifth step, in which lithium metal, an alkyllithium, or magnesium metal is caused to act on the vinyl halide compound (11) to prepare a vinyllithium compound or vinyl Grignard reagent and this reaction product is subjected to coupling reaction with a phosphorus halide compound (12) to obtain a 2,2-(diaryl)vinylphosphine compound (1) of the invention, use can be made of the ordinary coupling reaction of a lithium reagent or Grignard reagent with a phosphorus halide compound.

The amount of the lithium metal, alkyllithium, or magnesium metal to be used is preferably about from 0.5 to 3.0 mol, more preferably about from 0.8 to 1.5 mol, per mol of the vinyl halide compound (11).

The amount of the halogenated phosphorus compound (12) to be used is preferably about from 0.5 to 3.0 mol, more preferably about from 0.7 to 1.5 mol, per mol of the vinyl halide compound (11).

Examples of reaction solvents include ether solvents such as diethyl ether, diisopropyl ether, tetrahydrofuran, dimethoxyethane, dioxane, and 1,3-dioxolane. Preferred of these are diethyl ether and tetrahydrofuran. Such a solvent may be used in an amount of preferably about from 1.0 to 50 times by volume, more preferably about from 4.0 to 30 times by volume, the amount of the vinyl halide compound (11).

Appropriate additives may be added in conducting in this reaction in order to accelerate the reaction. Examples of the additives include copper chloride, copper bromide, copper iodide, copper triflate, copper cyanide, a copper iodide-dimethyl sulfide complex, a copper iodide-triphenylphosphine complex, and a copper iodide-tributylphosphine complex. Preferred of these are copper chloride, copper bromide, and copper iodide. The amount of such additives to be used is preferably about from 0.01 to 10 mol, more preferably about from 0.05 to 3.0 mol, per mol of the vinyl halide compound (11).

This reaction is usually conducted under an inert gas atmosphere such as nitrogen gas or argon gas. In this reaction, the reaction time is generally about from 10 minutes to 40 hours, preferably about from 30 minutes to 24 hours, and the reaction temperature is generally about from −100 to 120° C., preferably about from −80 to 80° C. Although such conditions can be used to carry out the reaction, they may be suitably varied according to the kinds and amounts of the vinyl halide compound (11) and phosphorus halide compound (12) to be used, etc.

After completion of the reaction, an ordinary post-treatment is conducted, whereby the target compound can be obtained.

The compound (1) of the invention thus obtained serves as a ligand to form a palladium-phosphine catalyst in cooperation with a palladium compound.

The palladium compound to be used as a catalyst precursor for forming the palladium-phosphine catalyst is not particularly limited. However, salts or complexes of palladium having a valence of 4, 2, or 0 are mainly used.

Specific examples of the palladium compound include compounds of tetravalent palladium, such as sodium hexachloropalladate(IV) tetrahydrate and potassium hexachloropalladate(IV), compounds of bivalent palladium, such as palladium(II) chloride, palladium(II) bromide, palladium (II) acetate, palladium(II) acetylacetonate, dichlorobis(benzonitrile)palladium(II), dichlorobis(acetonitrile)palladium(II), dichlorobis(triphenylphosphine)palladium(II), dichlorotetraamminepalladium(II), dichloro(cycloocta-1,5-diene)palladium(II), palladium(II) trifluoroacetate, and π-allylpalladium(II) chloride dimer, and compounds of zero-valent palladium, such as tris(dibenzylideneacetone)dipalladium(0), tris(dibenzylideneacetone)dipalladium(0)-chloroform complex, and tetrakis(triphenylphosphine)palladium(0).

The palladium-phosphine catalyst obtained by causing a palladium compound to act on the novel 2,2-(diaryl)vinylphosphine compound (1) can be prepared, for example, by reacting the 2,2-(diaryl)vinylphosphine compound (1) with π-allylpalladium(II) chloride dimer according to the method described in Y. Uozumi and T. Hayashi, *J. Am. Chem. Soc.*, 1991, Vol.113, p.9887.

The palladium-phosphine catalyst thus obtained by causing a palladium compound to act on the novel 2,2-(diaryl) vinylphosphine compound (1) of the invention can be used as a catalyst in the amination reaction or the carbon-carbon bond formation reaction in which an aryl compound having a leaving group is reacted with this reaction substance (an amine compound, an arylboric acid compound, an arylborate ester compound, or an alkyne compound) in the presence of a base.

The aryl compound having a leaving group in the invention is represented by general formula (2):

$$ArX^1 \qquad (2)$$

(wherein Ar is an aryl group which may have one or more substituents or a heteroaryl group which may have one or more substituents; and $X^1$ is a halogen atom, a trifluoromethanesulfonyloxy group, a methanesulfonyloxy group, or a toluenesulfonyloxy group).

The aryl compound (2) to be used in the invention is not particularly limited. Examples thereof include aryl bromides, aryl chlorides, aryl iodides, aryl fluorides, aryl trifluoromethanesulfonate, aryl methanesulfonate, aryl p-toluenesulfonate, and aryl halides having two or more halogen atoms.

Specific examples of the aryl compound (2) include: aryl bromides such as bromobenzene, o-bromoanisole, m-bromoanisole, p-bromoanisole, o-bromotoluene, m-bromotoluene, p-bromotoluene, o-bromophenol, m-bromophenol, p-bromophenol, 2-bromobenzotrifluoride, 3-bromobenzotrifluoride, 4-bromobenzotrifluoride, 1-bromo-2,4-dimethoxybenzene, 1-bromo-2,5-dimethoxybenzene, 2-bromophenethyl alcohol, 3-bromophenethyl alcohol, 4-bromophenethyl alcohol, 5-bromo-1,2,4-trimethylbenzene, 2-bromo-m-xylene, 2-bromo-p-xylene, 3-bromo-o-xylene, 4-bromo-o-xylene, 4-bromo-m-xylene, 5-bromo-m-xylene, 1-bromo-3-(trifluoromethoxy)benzene, 1-bromo-4-(trifluoromethoxy)benzene, 2-bromobiphenyl, 3-bromobiphenyl, 4-bromobiphenyl, 4-bromo-1,2-(methylenedioxy)benzene, 1-bromonaphthalene, 2-bromonaphthalene, 1-bromo-2-methylnaphthalene, 1-bromo-4-methylnaphthalene, 1,4-dibromonaphthalene, 4,4'-dibromobiphenyl, 2-bromothiophene, 3-bromothiophene, 2-bromopyridine, 3-bromopyridine, 4-bromopyridine, 9-bromophenanthrene, 2-bromofuran, and 3-bromofuran;

aryl chlorides such as chlorobenzene, o-chloroanisole, m-chloroanisole, p-chloroanisole, o-chlorotoluene, m-chlorotoluene, p-chlorotoluene, o-chlorophenol, m-chlorophenol, p-chlorophenol, 2-chlorobenzotrifluoride, 3-chlorobenzotrifluoride, 4-chlorobenzotrifluoride, 1-chloro-2,4-dimethoxybenzene, 1-chloro-2,5-dimethoxybenzene, 2-chlorophenethyl alcohol, 3-chlorophenethyl alcohol, 4-chlorophenethyl alcohol, 5-chloro-1,2,4-trimethylbenzene, 2-chloro-m-xylene, 2-chlorop-xylene, 3-chloro-o-xylene, 4-chloro-o-xylene, 4-chloro-m-xylene, 5-chloro-m-xylene, 1-chloro-3-(trifluoromethoxy)benzene, 1-chloro-4-(trifluoromethoxy)benzene, 2-chlorobiphenyl, 3-chlorobiphenyl, 4-chlorobiphenyl, 1-chloronaphthalene, 2-chloronaphthalene, 1-chloro-2-methylnaphthalene, 1-chloro-4-methylnaphthalene, 1,4-dichloronaphthalene, 4,4'-dichlorobiphenyl, 2-chlorothiophene, 3-chlorothiophene, 2-chloropyridine, 3-chloropyridine, 4-chloropyridine, 9-chlorophenanthrene, 2-chlorofuran, and 3-chlorofuran;

aryl iodides such as iodobenzene, o-iodoanisole, m-iodoanisole, p-iodoanisole, o-iodotoluene, m-iodotoluene, p-iodotoluene, o-iodophenol, m-iodophenol, p-iodophenol, 2-iodobenzotrifluoride, 3-iodobenzotrifluoride, 4-iodobenzotrifluoride, 1-iodo-2,4-dimethoxybenzene, 1-iodo-2,5-dimethoxybenzene, 2-iodophenethyl alcohol, 3-iodophenethyl alcohol, 4-iodophenethyl alcohol, 5-iodo-1,2,4-trimethylbenzene, 2-iodo-m-xylene, 2-iodo-p-xylene, 3-iodo-o-xylene, 4-iodo-o-xylene, 4-iodo-m-xylene, 5-iodom-xylene, 1-iodo-3-(trifluoromethoxy)benzene, 1-iodo-4(trifluoromethoxy)benzene, 2-iodobiphenyl, 3-iodobiphenyl, 4-iodobiphenyl, 1-iodonaphthalene, 2-iodonaphthalene, 1-iodo-2-methylnaphthalene, 1-iodo-4-methylnaphthalene, 1,4-diiodonaphthalene, 4,4'-diiodobiphenyl, 2-iodothiophene, 3-iodothiophene, 2-iodopyridine, 3-iodopyridine, 4-iodopyridine, 9-iodophenanthrene, 2-iodofuran, and 3-iodofuran;

aryl fluorides such as fluorobenzene, o-fluoroanisole, m-fluoroanisole, p-fluoroanisole, o-fluorotoluene, m-fluorotoluene, p-fluorotoluene, o-fluorophenol, m-fluorophenol, p-fluorophenol, 2-fluorobenzotrifluoride, 3-fluorobenzotrifluoride, 4-fluorobenzotrifluoride, 1-fluoro-2,4-dimethoxybenzene, 1-fluoro-2,5-dimethoxybenzene, 2-fluorophenethyl alcohol, 3-fluorophenethyl alcohol, 4-fluorophenethyl alcohol, 5-fluoro-1,2,4-trimethylbenzene, 2-fluoro-m-xylene, 2-fluoro-p-xylene, 3-fluoro-o-xylene, 4-fluoro-o-xylene, 4-fluorom-xylene, 5-fluoro-m-xylene, 1-fluoro-3-(trifluoromethoxy)benzene, 1-fluoro-4-(trifluoromethoxy)benzene, 2-fluorobiphenyl, 3-fluorobiphenyl, 4-fluorobiphenyl, 4-fluoro-1,2-(methylenedioxy) benzene, 1-fluoronaphthalene, 2-fluoronaphthalene, 1-fluoro-2-methylnaphthalene, 1-fluoro4-methylnaphthalene, 1,4-difluoronaphthalene, 4,4'-difluorobiphenyl, 2-fluorothiophene, 3-fluorothiophene, 2-fluoropyridine, 3-fluoropyridine, 4-fluoropyridine, 9-fluorophenanthrene, 2-fluorofuran, and 3-fluorofuran;

aryl trifluoromethanesulfonate such as trifluoromethanesulfonyloxybenzene, o-trifluoromethanesulfonyloxyanisole, m-trifluoromethanesulfonyloxyanisole, p-trifluoromethanesulfonyloxyanisole, o-trifluoromethanesulfonyloxytoluene, m-trifluoromethanesulfonyloxytoluene, p-trifluoromethanesulfonyloxytoluene, o-trifluoromethanesulfonyloxyphenol, m-trifluoromethanesulfonyloxyphenol, p-trifluoromethanesulfonyloxyphenol, 2-trifluoromethanesulfonyloxybenzotrifluoride, 3-trifluoromethanesulfonyloxybenzotrifluoride, 4-trifluoromethanesulfonyloxybenzotrifluoride, 1-trifluoromethanesulfonyloxy-2,4-dimethoxybenzene, 1-trifluoromethanesulfonyloxy-2,5-dimethoxybenzene, 2-trifluoromethanesulfonyloxyphenethyl alcohol, 3-trifluoromethanesulfonyloxyphenethyl alcohol, 4-trifluoromethanesulfonyloxyphenethyl alcohol, 5-trifluoromethanesulfonyloxy-1,2,4-trimethylbenzene, 2-trifluoromethanesulfonyloxy-m-xylene, 2-trifluoromethanesulfonyloxy-p-xylene, 3-trifluoromethanesulfonyloxy-o-xylene, 4-trifluoromethanesulfonyloxy-o-xylene, 4-trifluoromethanesulfonyloxy-m-xylene, 5-trifluoromethanesulfonyloxy-m-xylene, 1-trifluoromethanesulfonyloxy-3-(trfluoromethoxy) benzene, 1-trifluoromethanesulfonyloxy-4-(trifluoromethoxy)benzene, 2-trifluoromethanesulfonyloxybiphenyl, 3-trifluoromethanesulfonyloxybiphenyl, 4-trifluoromethanesulfonyloxybiphenyl, 4-trifluoromethanesulfonyloxy-1,2-(methylenedioxy) benzene, 1-trifluoromethanesulfonyloxynaphthalene, 2-trifluoromethanesulfonyloxynaphthalene, 1-trifluoromethanesulfonyloxy-2-methylnaphthalene, 1-trifluoromethanesulfonyloxy-4-methylnaphthalene, 1,4-ditrifluoromethanesulfonyloxynaphthalene, 4,4'-ditrifluoromethanesulfonyloxybiphenyl, 2-trifluoromethanesulfonyloxythiophene, 3-trifluoromethanesulfonyloxythiophene, 2-trifluoromethanesulfonyloxypyridine, 3-trifluoromethanesulfonyloxypyridine, 4-trifluoromethanesulfonyloxypyridine, 9-trifluoromethanesulfonyloxyphenanthrene, 2-trifluoromethanesulfonyloxyfuran, and 3-trifluoromethanesulfonyloxyfuran;

aryl methanesulfonate such as methanesulfonyloxybenzene, o-methanesulfonyloxyanisole, m-methanesulfonyloxyanisole, p-methanesulfonyloxyanisole, o-methanesulfonyloxytoluene, m-methanesulfonyloxytoluene, p-methanesulfonyloxytoluene, o-methanesulfonyloxyphenol, m-methanesulfonyloxyphenol, p-methanesulfonyloxyphenol, 2-methanesulfonyloxybenzotrifluoride, 3-methanesulfonyloxybenzotrifluoride, 4-methanesulfonyloxybenzotrifluoride, 1-methanesulfonyloxy-2,4-dimethoxybenzene, 1-methanesulfonyloxy-2,5-dimethoxybenzene, 2-methanesulfonyloxyphenethyl alcohol, 3-methanesulfonyloxyphenethyl alcohol, 4-methanesulfonyloxyphenethyl alcohol, 5-methanesulfonyloxy-1,2,4-trimethylbenzene, 2-methanesulfonyloxy-m-xylene, 2-methanesulfonyloxy-p-xylene, 3-methanesulfonyloxy-o-xylene, 4-methanesulfonyloxy-o-xylene, 4-methanesulfonyloxy-mxylene, 5-methanesulfonyloxy-m-xylene, 1-methanesulfonyloxy-3-(trifluoromethoxy)benzene, 1-methanesulfonyloxy-4-(trifluoromethoxy)benzene, 2-methanesulfonyloxybiphenyl, 3-methanesulfonyloxybiphenyl, 4-methanesulfonyloxybiphenyl, 4-methanesulfonyloxy-1,2(methylenedioxy)benzene, 1-methanesulfonyloxynaphthalene, 2-methanesulfonyloxynaphthalene, 1-methanesulfonyloxy-2-methylnaphthalene, 1-methanesulfonyloxy-4-methylnaphthalene, 1,4-dimethanesulfonyloxynaphthalene, 4,4'-dimethanesulfonyloxybiphenyl, 2-methanesulfonyloxythiophene, 3-methanesulfonyloxythiophene, 2-methanesulfonyloxypyridine, 3-methanesulfonyloxypyridine, 4-methanesulfonyloxypyridine, 9-methanesulfonyloxyphenanthrene, 2-methanesulfonyloxyfuran, and 3-methanesulfonyloxyfuran; and aryl p-toluenesulfonate such as p-toluenesulfonyloxybenzene, o-(p-toluenesulfonyloxy)anisole, m-(p-toluenesulfonyloxy)anisole, p-(p-toluenesulfonyloxy)anisole, o-(p-toluenesulfonyloxy)toluene, m-(p-toluenesulfonyloxy)toluene, p-(p-toluenesulfonyloxy)toluene, o-(p-toluenesulfonyloxy)phenol, m-(p-toluenesulfonyloxy)phenol, p-(p-toluenesulfonyloxy)phenol, 2-(p-toluenesulfonyloxy)benzotrifluoride, 3-(p-toluenesulfonyloxy)benzotrifluoride, 4-(p-toluenesulfonyloxy)benzotrifluoride, 1-(p-toluenesulfonyloxy)-2,4-dimethoxybenzene, 1-(p-toluenesulfonyloxy)-2,5-dimethoxybenzene, 2-(p-toluenesulfonyloxy)phenethyl alcohol, 3-(p-toluenesulfonyloxy)phenethyl alcohol, 4-(p-toluenesulfonyloxy)phenethyl alcohol, 5-(p-toluenesulfonyloxy)-1,2,4-trimethylbenzene, 2-(p-toluenesulfonyloxy)-m-xylene, 2-(p-toluenesulfonyloxy)-p-xylene, 3-(p-toluenesulfonyloxy)-o-xylene, 4-(p-toluenesulfonyloxy)-o-xylene, 4-(p-toluenesulfonyloxy)-m-xylene, 5-(p-toluenesulfonyloxy)-m-xylene, 1-(p-toluenesulfonyloxy)-3-(trifluoromethoxy)benzene, 1-(p-toluenesulfonyloxy)-4-(trifluoromethoxy) benzene, 2-(p-toluenesulfonyloxy)biphenyl, 3-(p-toluenesulfonyloxy)biphenyl, 4-(p-toluenesulfonyloxy)biphenyl, 4-(p-toluenesulfonyloxy)-1,2-(methylenedioxy)benzene, 1-(p-toluenesulfonyloxy)naphthalene, 2-(p-toluenesulfonyloxy)naphthalene, 1-(p-toluenesulfonyloxy)-2-methylnaphthalene, 1-(p-toluenesulfonyloxy)-4-methylnaphthalene, 1,4-di(p-toluenesulfonyloxy)naphthalene, 4,4'-di(p-toluenesulfonyloxy)biphenyl, 2-(p-toluenesulfonyloxy)thiophene, 3-(p-toluenesulfonyloxy)thiophene, 2-(p-toluenesulfonyloxy)pyridine, 3-(p-toluenesulfonyloxy)pyridine, 4-(p-toluenesulfonyloxy)pyridine, 9-(p-toluenesulfonyloxy)phenanthrene, 2-(p-toluenesulfonyloxy)furan, and 3-(p-toluenesulfonyloxy)furan.

Other examples of aryl halides which can be used in the invention include aryl halides having two or more halogen atoms, such as 1,2-dibromobenzene, 1,3-dibromobenzene, 1,4-dibromobenzene, 9,10-dibromoanthracene, 9,10-dichloroanthracene, 1-bromo-2-fluorobenzene, 1-bromo-3-fluorobenzene, 1-bromo-4-fluorobenzene, 2-bromo-chlorobenzene, 3-bromo-chlorobenzene, 4-bromo-chlorobenzene, 2-bromo-5-chlorotoluene, 3-bromo-4-chlorobenzotrifluoride, 5-bromo-2-chlorobenzotrifluoride, 1-bromo-2,3-dichlorobenzene, 1-bromo-2,6-dichlorobenzene, 1-bromo-3,5-dichlorobenzene, 2-bromo-4-fluorotoluene, 2-bromo-5-fluorotoluene, 3-bromo-4-fluorotoluene, 4-bromo-2-fluorotoluene, and 4-bromo-3-fluorotoluene.

Examples of the amine compound to be used in the invention include primary amines, secondary amines, imines, and amides.

The primary amines are not particularly limited. Examples thereof include aliphatic primary amines such as ethylamine, propylamine, butylamine, isobutylamine, tertbutylamine, pentylamine, cyclopentylamine, hexylamine, cyclohexylamine, heptylamine, and octylamine; and aromatic primary amines such as aniline, o-fluoroaniline, mfluoroaniline, p-fluoroaniline, o-anisidine, m-anisidine, p-anisidine, o-toluidine, m-toluidine, p-toluidine, 2-naphthylamine, 2-aminobiphenyl, 4-aminobiphenyl, 3,4-methylenedioxyaniline, m-xylidine, and p-xylidine.

The secondary amines are not particularly limited. Examples thereof include cyclic secondary amines such as piperazine, 2-methylpiperazine, homopiperazine, N-methylhomopiperazine, 2,6-dimethylpiperazine, N-methylpiperazine, N-ethylpiperazine, N-ethoxycarbonylpiperazine, N-benzylpiperazine, morpholine, 2,6-dimethylmorpholine, piperidine, 2,6-dimethylpiperidine, 3,3-dimethylpiperidine, 3,5-dimethylpiperidine, 2-ethylpiperidine, 4-piperidone, pyrrolidine, 2,5-dimethylpyrrolidine, carbazole, indole, and indoline; and noncyclic secondary amines such as dimethylamine, diethylamine, and other noncyclic secondary amines which may have one or more substituents on the aromatic ring(s), such as N-methylaniline, N-ethylaniline, N-methylbenzylamine, N-methylphenethylamine, and diphenylamine derivatives.

The imines are not particularly limited. Examples thereof include benzophenonimine and 4,4'-dimethoxybenzophenoneimine.

The amides are not particularly limited. Examples thereof include 2-azetidinone (β-propiolactam), γ-butyrolactam, δ-valerolactam, ε-caprolactam, acetamide, propionamide, cyclohexanecarboxamide, benzamide, N-methylformamide, N-methylacetamide, N-ethylacetamide, N-methylcyclohexanecarboxamide, and N-methylbenzamide.

The arylboric acid compounds and the arylborate ester compounds to be used in the invention are not particularly limited. Examples thereof include phenylboric acid, 4-methylphenylboric acid, 2-thienylboric acid, 2-furylboric acid, 2,3,4,5,6-pentafluorophenylboric acid, 2-fluorophenylboric acid, 3-fluorophnylboric acid, 4-fluorophenylboric acid, 2-chlorophenylboric acid, 3-chlorophenylboric acid, 4-chlorophenylboric acid, 2-bromophenylboric acid, 3-bromophenylboric acid, 4-bromophenylboric acid, 2-iodophenylboric acid, 3-iodophenylboric acid, 4-iodophenylboric acid, 2,4-difluorophenylboric acid, 2,5-difluorophenylboric acid, 2,6-difluorophenylboric acid, 3,4-difluorophenylboric acid, 3,5-difluorophenylboric acid, 4-trifluoromethylphenylboric acid, 3,5-bis(trifluoromethyl)phenylboric acid, 3-cyanophenylboric acid, 4-formylphenylboric acid, 4-methoxyphenylboric acid, 1-naphthylboric acid, 2-naphthylboric acid, ferrocenylboric acid, 4-hydroxyphenylboric acid, and the aryl borate ester compound (such as dimethyl, diethyl, dipropyl, diisoprpyl and pinacol ester) of the arylboric acid compound as defined above.

The arylalkyne compounds to be used in the invention are not particularly limited. Examples thereof include acetylene, propyne, 1-butyne, 1-pentyne, 1-hexyne, 1-heptyne, 1-octyne, phenylacetylene, 2-propyn-1-ol, 3-butyn-1-ol, 2-methyl-3-butyn-2-ol, 1-ethynyl-cyclohexanol, and trimethylsilylacetylene.

In the invention, the amine compound may be used so as to be present in the reaction system in an amount of from 0.1 to 50 mol per mol of the aryl compound (2) or in an amount of from 0.1 to 50 mol per mol of the leaving group on the ring structure of the aryl compound (2). However, from the standpoint of facilitating the recovery of the amine compound remaining unreacted, the amine compound is preferably used so as to be present in the reaction system in an amount of from 0.2 to 30 mol per mol of the aryl compound (2) or in an amount of from 0.2 to 60 mol per mol of the leaving group on the ring structure of the aryl compound (2).

In the invention, the aryl boric acid compound or aryl borate ester compound may be used so as to be present in the reaction system in an amount of from 0.1 to 50 mol per mol of the aryl compound (2) or in an amount of from 0.1 to 50 mol per of the leaving group on the ring structure of the aryl compound (2). However, from the standpoint of facilitating the recovery of the aryl boric acid compound or aryl borate ester compound remaining unreacted, the aryl boric acid compound or aryl borate ester compound is preferably used so as to be present in the reaction system in an amount of from 0.2 to 30 mol per mol of the aryl compound (2) or in an amount of from 0.2 to 60 mol per mol of the leaving group on the ring structure of the aryl compound (2).

In the invention, the alkyne compound may be used so as to be present in the reaction system in an amount of from 0.1 to 50 mol per mol of the aryl compound (2) or in an amount of from 0.1 to 50 mol per of the leaving group on the ring structure of the aryl compound (2). However, from the standpoint of facilitating the recovery of the alkyne compound remaining unreacted, the aryl boric acid compound or aryl borate ester compound is preferably used so as to be present in the reaction system in an amount of from 0.2 to 30 mol per mol of the aryl compound (2) or in an amount of from 0.2 to 60 mol per mol of the leaving group on the ring structure of the aryl compound (2).

The base to be used in the invention is not particularly limited, and may be selected from inorganic bases and/or organic bases. Preferred examples thereof include alkali metal fluorides such as lithium fluoride, sodium fluoride, potassium fluoride, rubidium fluoride, and cesium fluoride; alkali metal or alkaline earth metal carbonates such as lithium carbonate, sodium carbonate, potassium carbonate, rubidium carbonate, cesium carbonate, magnesium carbonate, calcium carbonate, and barium carbonate; alkali metal alkoxides such as sodium methoxide, sodium ethoxide, sodium phenoxide, potassium methoxide, potassium ethoxide, potassium phenoxide, lithium phenoxide, lithium tert-butoxide, sodium tert-butoxide, and potassium tert-butoxide; alkali metal phosphates such as lithium phosphate, potassium phosphate, and sodium phosphate; and tertiary amines such as triethylamine, tripropylamine, triisopropylamine, tributylamine, tricyclohexylamine; and secondary amines such as diethylamine, dipropylamine, diisopropylamine, dibutylamine, and dicyclohexylamine. Besides being added as it is to the reaction system, such as a base may be supplied to the reaction system by in situ preparing it from an alkali metal, alkali metal hydride, alkali metal hydroxide, or alkali metal phosphate and an alcohol.

The amount of the base to be used is preferably at least 0.5 mol per mol of the leaving group of the aryl compound (2). If the amount of the base is smaller than 0.5 mol, there are cases where the yield of an arylamine, a diaryl and an arylalkyne is reduced. Even when the base is added in large excess, the yield of an arylamine, a diaryl and an arylalkyne remains unchanged, resulting only in a complicated post-treatment after completion of the reaction. Consequently, the amount of the base to be added is more preferably in the range of from 1 to 5 mol.

The reaction according to the invention is usually conducted in the presence of an inert solvent. The solvent to be used is not particularly limited as long as it does not considerably inhibit the reaction. Examples thereof include aliphatic organic solvents such as pentane, hexane, heptane, and octane; alicyclic organic solvents such as cyclohexane and methylcyclohexane; aromatic organic solvents such as benzene, toluene, and xylene; ether type organic solvents such as diethyl ether, diisopropyl ether, dimethoxyethane, tetrahydrofuran, dioxane, and dioxolane; and acetonitrile, dimethylformamide, dimethyl sulfoxide, and hexamethylphosphoric triamide. Preferred of these are aromatic organic solvents such as benzene, toluene, and xylene and ether type organic solvents such as diethyl ether, dimethoxyethane, tetrahydrofuran, and dioxane.

In this reaction, the catalyst produces the same results when used by any of the following methods: a) a method in which a palladium compound; a base; an amine compound, an arylboric acid compound, an arylborate ester compound, or an alkyne compound; an aryl compound havng a leaving group; and the 2,2-(diaryl)vinylphosphine compound (1), which each has been described above, are charged into a reactor simultaneously; b) a method in which a palladium compound, the reaction substrate, and the 2,2-(diaryl) vinylphosphine compound (1) are separately charged into a reactor in the presence of a base; c) a method in which a palladium compound is mixed beforehand with the 2,2-(diaryl)vinylphosphine compound (1) in a reaction system to prepare a catalyst, and an aryl compound having a leaving group is then added to the reaction system in the presence of a base; and d) a method in which a palladium compound is mixed beforehand with the 2,2-(diaryl)vinylphosphine compound (1) to prepare a catalyst, and this catalyst and an aryl compound having a leaving group and this reaction substance are separately charged into a reactor.

The amount of the palladium compound to be used for the amination reaction or the carbon-carbon bond formation reaction is generally from 0.001 to 20 mol %, preferably from 0.01 to 5 mol %, based on this reaction substance (the amine compound, the arylboric acid compound, the arylborate ester compound, or the alkyne compound). The amount of the 2,2-(diaryl)vinylphosphine compound to be used for this reaction is generally from 0.1 to 10 times by mol, preferably from 1 to 5 times by mol, the amount of the palladium compound.

In the invention, a palladium compound and the 2,2-(diaryl)vinylphosphine compound (1) are indispensable.

The amination reaction or the carbon-carbon bond formation reaction according to the invention may be conducted at ordinary pressure under an inert gas atmosphere such as nitrogen or argon, or may be conducted at an elevated pressure.

The reaction according to the invention may be conducted at a temperature of generally from 10 to 300° C., preferably from 20 to 200° C.

Although the reaction time in the invention varies depending on the amounts of the aryl compound (2), this reaction substance (the amine compound, the arylboric acid compound, the arylborate ester compound, or the alkyne compound), base, palladium compound, and 2,2-(diaryl) vinylphosphine compound (1) and on the reaction temperature, it may be selected in the range of from several minutes to 72 hours.

After completion of the reaction, the reaction mixture is treated in an ordinary way, whereby the target compound can be obtained.

The novel 2,2-(diaryl)vinylphosphine compound of the invention, when used together with a palladium compound, serves as the catalyst of an amination reaction or a carbon-carbon bond formation reaction to show excellent performances. When this catalyst is used in the amination reaction or the carbon-carbon formation reaction of an aryl compound having a leaving group, an arylamine, a diaryl or an arylalkyne can be efficiently produced in a shorter time period than in the amination reaction or the carbon-carbon bond formation reaction with any conventional amination catalyst or any conventional carbon-carbon bond formation reaction catalyst. It is hence an excellent catalyst for industrial use.

The invention will be explained below in more detail by reference to Examples. However, the invention should not be construed as being limited by these Examples in any way.

In the Examples, properties were determined using the following apparatus.

1) $^1$H-NMR Spectrometry: Apparatus Type GEMINI 2000 (manufactured by Varian) or apparatus Type DRX-500 (manufactured by Varian).

Internal standard substance: tetramethylsilane

2) $^{31}$P-NMR Spectrometry: Apparatus Type DRX-500 (manufactured by Bruker)

External standard substance: 85% phosphoric acid

3) $^{19}$F-NMR Spectrometry: Apparatus Type DRX-500 (manufactured by Bruker)

Internal standard substance: trifluoroacetic acid

4) Melting Point: Yanaco MP-500D (manufactured by Yanagimoto Shoji K.K.)

5) Gas Chromatograph: GC 353 (manufactured by GL Science)

Column: NB-1 (30 m×0.25 mm) (manufactured by GL Science)

Internal standard substance: o-terphenyl or tridecane

6) Mass Spectrometry (MS):

Mass spectrometer M-80: Ionization voltage, 20 eV (manufactured by Hitachi Ltd.)

EXAMPLE 1

Synthesis of 1,1-Diphenyl-2-(diphenylphosphino) propene (Exemplified Compound 20)

(1) Synthesis of 1-Diphenylpropene

Into a reactor were introduced 96.0 g (3.95 mol) of magnesium and 500 mL of tetrahydrofuran (hereinafter abbreviated as THF) under a nitrogen atmosphere. Iodine and bromobenzene were added to the mixture in a slight amount to ascertain initiation of a reaction. Thereafter, a mixture of 677 g (4.31 mol) of bromobenzene and 1,500 mL of THF was gradually added dropwise thereto while keeping the temperature of the system at about 40° C., and this mixture was refluxed for 1 hour. Thereto was gradually added dropwise 140 g (1.59 mol) of methyl propionate while keeping the temperature of the system at about 40° C. This mixture was stirred at 60° C. for 3 hours. The resultant reaction mixture was washed with 0.1 M hydrochloric acid, saturated aqueous sodium hydrogen carbonate solution, and saturated aqueous sodium chloride solution and then dried with anhydrous magnesium sulfate. Thereafter, the solvent was removed under reduced pressure. The concentrate was dissolved in 800 mL of toluene, and 3.8 g of p-toluenesulfonic acid monohydrate was added thereto. Azeotropic dehydration was conducted for 1.5 hours with toluene refluxing. After being cooled, the reaction mixture was washed with saturated aqueous sodium hydrogen carbonate solution and saturated aqueous sodium chloride solution and then dried with anhydrous magnesium sulfate. Thereafter, the solvent was removed under reduced pressure. The resultant concentrate was recrystallized from methanol to obtain 230 g (75%) of the target compound as white crystals.

Melting point: 48–49° C.; $^1$H-NMR (CDCl$_3$) δ 1.76 (d, J=7.1 Hz, 3H), 6.17 (q, J=7.1 Hz, 1H), 7.08–7.44 (m, 10H).

(2) Synthesis of 2-Bromo-1,1-diphenylpropene

Into a reactor were introduced 19.4 g (100 mmol) of the 1,1-diphenylpropene and 78 mL of 1,2-dichloroethane under a nitrogen atmosphere. The contents were cooled to 0° C., and 15.9 g (100 mmol) of bromine was gradually added dropwise thereto. The resultant mixture was stirred at room temperature for 1 hour. Thereafter, 32.4 mL (400 mmol) of pyridine and 156 mL of toluene were added thereto and this mixture was stirred at 80° C. for 3 hours. After being cooled, the reaction mixture was washed with saturated aqueous sodium hydrogen carbonate solution and saturated aqueous sodium chloride solution and then dried with anhydrous magnesium sulfate. Thereafter, the solvent was removed under reduced pressure. The concentrate was purified by column chromatography and then recrystallized from methanol to obtain 14.5 g (53%) of the target compound as white crystals.

Melting point: 46–47° C.; $^1$H-NMR (CDCl$_3$) δ 2.43 (s, 3H), 7.14–7.38 (m, 10H).

(3) Synthesis of 1,1-Diphenyl-2-(diphenylphosphino) propene (Exemplified Compound 20)

Into a reactor were introduced 1.37 g (5.00 mmol) of the 2-bromo-1,1-diphenylpropene and 14 mL of THF under a nitrogen atmosphere. The contents were cooled to −70° C., and 3.4 mL (5.5 mmol; 1.6 M hexane solution) of butyllithium was gradually added dropwise thereto. The resultant mixture was stirred for 30 minutes. Thereafter, 1.1 mL (6.0 mmol) of chlorodiphenylphosphine was added, and this mixture was heated to room temperature and then stirred for 13 hours. Water was added to the reaction mixture. The organic layer was extracted with ethyl acetate, and the extract was dried with anhydrous magnesium sulfate. Thereafter, the solvent was removed under reduced pressure. The concentrate was recrystallized from ethanol to obtain 1.08 g (60%) of the target compound as white crystals.

Melting point: 128–130° C.; $^1$H-NMR (CDCl$_3$) δ 1.70 (d, J=2.8 Hz, 3H), 7.12–7.47 (m, 20H); $^{31}$P-NMR (CDCl$_3$) δ −4.68.

EXAMPLE 2

Synthesis of 1,1-Diphenyl-2-(dicyclohexylphosphino)propene (Exemplified Compound 19)

Into a reactor were introduced 8.50 g (31.1 mmol) of the 2-bromo-1,1-diphenylpropene obtained in Example 1 (2) and 85 ml of THF under a nitrogen atmosphere. The contents were cooled to −70° C. Thereto was gradually added dropwise 21.4 mL (34.2 mmol; 1.6 M hexane solution) of butyllithium. The resultant mixture was stirred for 30 minutes. Thereafter, 8.25 mL (37.3 mmol) of chlorodicyclohexylphosphine was added, and this mixture was stirred for 75 minutes, subsequently heated to room temperature, and then further stirred for 15.5 hours. Water was added to the reaction mixture. The organic layer was extracted with ethyl acetate, and the extract was dried with anhydrous magnesium sulfate. Thereafter, the solvent was removed under reduced pressure. The concentrate was recrystallized from ethanol to obtain 8.80 g (72%) of the target compound as white crystals.

Melting point: 128–130° C.; $^1$H-NMR (CDCl$_3$) δ 1.06–1.94 (m, 25H), 7.04–7.36 (m, 10H); $^{31}$P-NMR (CDCl$_3$) δ −3.68.

EXAMPLE 3

Synthesis of 1,1-Diphenyl-2-(di-tert-butylphosphino)propene (Exemplified Compound 17)

Into a reactor were introduced 1.37 g (5.0 mmol) of the 2-bromo-1,1-diphenylpropene obtained in Example 1 (2), 0.134 g (5.5 mmol) of magnesium, and 11 mL of THF under a nitrogen atmosphere. Iodine and bromobenzene were added to the mixture in a slight amount to ascertain initiation of a reaction. Thereafter, the reaction mixture was refluxed for 2 hours and then cooled. Thereto were added 0.520 g (5.3 mmol) of copper chloride and 1.1 mL (5.5 mmol) of chlorodi-t-butylphosphine. This reaction mixture was refluxed for 18 hours and then cooled to room temperature. Thereto was added 14 mL of heptane. The crystals yielded were taken out by filtration and dissolved in 40 mL of ethyl acetate. The resultant solution was washed with 28% ammonia water and an aqueous sodium chloride solution and then dried with anhydrous magnesium sulfate. Thereafter, the solvent was removed under reduced pressure. The concentrate was recrystallized from ethanol to obtain 0.736 g (43%) of the target compound as white crystals.

Melting point: 130–133° C.; $^1$H-NMR (CDCl$_3$) δ 1.21 (s, 9H), 1.26 (s, 9H), 2.06 (d, J=1.4 Hz, 3H), 7.08–7.36 (m, 10H); $^{31}$P-NMR (CDCl$_3$) δ 30.13.

EXAMPLE 4

Synthesis of 1,1-Bis(4-dimethylaminophenyl)-2-(diphenylphosphino)propene (Exemplified Compound 105)

(1) Synthesis of 1,1-Bis(4-dimethylaminophenyl)propene

Into a reactor was introduced 102 mL (82.0 mmol; 0.80 M THF solution) of ethylmagnesium bromide under a nitrogen atmosphere. The contents were cooled to 0° C. Thereto was gradually added dropwise a solution prepared by mixing 20.0 g (74.5 mmol) of 4,4'-bis(dimethylamino) benzophenone and 40 mL of THF. This mixture was stirred at room temperature for 5 hours. Saturated aqueous ammonium chloride solution was added to the resultant reaction mixture, and the metal salt yielded was removed by Celite filtration. The organic layer was separated from the filtrate and then extracted with toluene. Thereafter, the solvent was removed under reduced pressure. The concentrate was dissolved in 150 mL of toluene, and 0.1 g of p-toluenesulfonic acid monohydrate was added thereto. Azeotropic dehydration was conducted with toluene refluxing. After being cooled, the reaction mixture was washed with saturated aqueous sodium hydrogen carbonate solution and saturated aqueous sodium chloride solution, subsequently dried with anhydrous magnesium sulfate, and then concentrated under reduced pressure. This concentrate was purified by column chromatography to obtain 13.6 g (65%) of light-yellow crystals. $^1$H-NMR (CDCl$_3$) δ 1.77 (d, J=7.0 Hz, 3H), 2.92 (s, 6H), 2.98 (s, 6H), 5.94 (q, J=7.0 Hz, 1H), 6.58–6.79 (m, 4H), 7.02–7.18 (m, 4H).

(2) Synthesis of 1,1-Bis(4-dimethylaminophenyl)-2-bromopropene

Into a reactor were introduced 13.6 g (48.5 mmol) of the 1,1-bis(4-dimethylaminophenyl)propene and 54 mL of 1,2-dichloroethane under a nitrogen atmosphere. The contents were cooled to 0° C. Thereto was gradually added dropwise 7.76 g (48.5 mmol) of bromine. The resultant mixture was stirred at room temperature for 2.5 hours. Thereafter, 15.7 mL (194 mmol) of pyridine and 109 mL of toluene were added thereto and this mixture was stirred at 80° C. for 3 hours. After being cooled, the reaction mixture was washed with saturated aqueous sodium hydrogen carbonate solution and saturated aqueous sodium chloride solution, subsequently dried with anhydrous magnesium sulfate, and then concentrated under reduced pressure. The concentrate was purified by column chromatography and then crystallized from methanol to obtain 12.0 g (69%) of the target compound as green-yellow crystals.

Melting point: 119–122° C.; $^1$H-NMR (CDCl$_3$) δ 2.46 (s, 3H), 2.94 (s, 12H), 6.58–6.70 (m, 4H), 6.96–7.20 (m, 4H).

(3) Synthesis of 1,1-Bis(4-dimethylaminophenyl)-2-(diphenylphosphino)propene (Exemplified Compound 105)

Into a reactor were introduced 3.0 g (8.3 mmol) of the 1,1-bis(4-dimethylaminophenyl)-2-bromopropene and 10 mL of THF under a nitrogen atmosphere. The contents were cooled to −60° C. Thereto was gradually added dropwise 5.2 mL (8.3 mmol; 1.6 M hexane solution) of butyllithium. The resultant mixture was stirred for 30 minutes. Thereafter, 1.1 mL (6.0 mmol) of chlorodiphenylphosphine was added thereto and this mixture was heated to room temperature and stirred for 16 hours. Water was added to the reaction mixture. The resultant mixture was extracted with ethyl acetate, and the extract was dried with anhydrous magnesium sulfate. Thereafter, the solvent was removed under reduced pressure. The concentrate was recrystallized twice from hexane/ethanol to obtain 1.9 g (60%) of the target compound as white crystals.

Melting point: 95–97° C.; $^1$H-NMR (CDCl$_3$) δ 1.73 (d, J=2.8 Hz, 3H), 2.91 (s, 6H) 2.95 (s, 6H), 6.52–6.69 (m, 4H), 6.97–7.10 (m, 4H), 7.187.49 (m, 10H); $^{31}$P-NMR (CDCl$_3$) δ −2.79.

EXAMPLE 5

Synthesis of 1,1-Bis(4-dimethylaminophenyl)-2-(dicyclohexylphosphino)propene (Exemplified Compound 120)

Into a reactor were introduced 1.44 g (4.00 mmol) of the 1,1-bis(4-dimethylaminophenyl)-2-bromopropene obtained in Example 4 (2) and 14 mL of THF under a nitrogen atmosphere. The contents were cooled to −60° C. Thereto was gradually added dropwise 2.8 mL (4.4 mmol; 1.6 M hexane solution) of butyllithium. The resultant mixture was stirred at that temperature for 1 hour. Thereafter, 0.97 mL (4.4 mmol) of chlorodicyclohexylphosphine was added thereto, and this mixture was stirred for 30 minutes, subsequently heated to room temperature, and then further stirred for 17 hours. Water was added to the reaction mixture. The organic layer was extracted with ethyl acetate, and the extract was dried with anhydrous magnesium sulfate. Thereafter, the solvent was removed under reduced pressure. The concentrate was recrystallized from ethanol and hexane to obtain 0.44 g (23%) of the target compound as white crystals.

Melting point: 159–164° C.; $^1$H-NMR (CDCl$_3$) δ 1.04–2.15 (m, 25H), 2.91 (s, 6H), 2.92 (s, 6H), 6.50–6.75 (m, 4H), 6.85–7.08 (m, 4H); $^{31}$P-NMR (CDCl$_3$) δ −2.19.

EXAMPLE 6

Synthesis of 1,1-Bis(4-dimethylaminophenyl)-2-(di-t-butylphosphino)propene (Exemplified Compound 118)

Into a reactor were introduced 1.44 g (4.00 mmol) of the 1,1-bis(4-dimethylaminophenyl)-2-bromopropene obtained in Example 4 (2), 0.107 g (4.4 mmol) of magnesium, and 11.5 mL of THF under a nitrogen atmosphere. A slight amount of iodine was added to the mixture to ascertain initiation of a reaction. Thereafter, the reaction mixture was refluxed for 2 hours and then cooled. Thereto were added 0.416 g (4.2 mmol) of copper chloride and 0.91 mL (4.4 mmol) of chlorodi-tert-butylphosphine. The reaction mixture was refluxed for 18 hours and then cooled to room temperature. Thereto were added 22.5 mL of heptane and 7.5 mL of diethyl ether. The crystals yielded were taken out by filtration and dissolved in 30 mL of ethyl acetate. The resultant solution was washed with 28% ammonia water and an aqueous sodium chloride solution and then dried with anhydrous magnesium sulfate. Thereafter, the solvent was removed under reduced pressure. The concentrate was recrystallized from ethanol to obtain 0.34 g (20%) of the target compound as white crystals.

Melting point: 133–135° C.; $^1$H-NMR (CDCl$_3$) δ 1.21 (s, 9H), 1.26 (s, 9H), 2.21 (d, J=1.6 Hz, 3H), 2.91 (s, 6H), 2.92 (s, 6H), 6.50–6.69 (m, 4H), 6.91–7.04 (m, 4H); $^{31}$P-NMR (CDCl$_3$) δ 31.68.

EXAMPLE 7

Synthesis of 2,2-Diphenyl-1-(diphenylphosphino)ethylene (Exemplified Compound 10)

(1) Synthesis of 1,1-Diphenylethylene

Into a reactor were introduced 31.6 g (1.30 mol) of magnesium and 50 mL of THF under a nitrogen atmosphere. Iodine and ethyl bromide were added to the mixture in a slight amount to ascertain initiation of a reaction. Thereafter, 600 mL of THF was added thereto, and methyl chloride gas having a regulated temperature was bubbled into the resultant mixture at a regulated rate so as to keep the mixture at 30 to 40° C. After heat generation ended and the magnesium metal was ascertained to have disappeared, the reaction mixture was stirred at that temperature for 1 hour. Subsequently, a mixture of 182 g (1.10 mol) of benzophenone and 364 mL of THF was gradually added dropwise thereto at 35 to 40° C. and this mixture was stirred for 15 hours. This reaction mixture was cooled and then poured into 10% aqueous ammonium chloride solution. The resultant mixture was stirred for 30 minutes. After liquid separation, the organic layer was washed with an aqueous sodium chloride solution and water, subsequently dried with anhydrous magnesium sulfate, and then concentrated under reduced pressure. To the concentrate were added 400 mL of toluene and 1 g of p-toluenesulfonic acid monohydrate. The resultant solution was subjected to azeotropic dehydration for 2 hours with toluene refluxing. After being cooled, the reaction mixture was washed with 2% aqueous sodium carbonate solution and water and then dried with anhydrous magnesium sulfate. Thereafter, the solvent was removed under reduced pressure. The concentrate was purified by distillation to obtain 174 g (97%) of the target compound.

Melting point: 103° C./134 Pa (1 mmHg).

(2) Synthesis of 1-Bromo-2,2-diphenylethylene

Into a reactor were introduced 110 g (0.60 mol) of the 1,1-diphenylethylene and 1,098 g of carbon tetrachloride under a nitrogen atmosphere. A solution prepared by mixing 95.9 g (0.60 mol) of bromine with 288 g of carbon tetrachloride was added dropwise thereto over 1 hour with cooling with ice. After completion of the addition, the reaction mixture was stirred at that temperature for 7 hours and then concentrated. To the residue were added 119 g of pyridine and 500 mL of toluene. This mixture was refluxed for 3 hours. After being cooled, the reaction mixture was washed with 5% hydrochloric acid and water, subsequently dried with anhydrous sodium sulfate, and then concentrated under reduced pressure. The resultant concentrate was distilled and then recrystallized from methanol to obtain 126 g (81%) of the target compound as white crystals.

Melting point: 45° C.; $^1$H-NMR (CDCl$_3$) δ 6.77 (s, 1H), 7.15–7.47 (m, 10H).

(3) Synthesis of 2,2-Diphenyl-1-(diphenylphosphino)ethylene (Exemplified Compound 10)

The same procedure as in Example 1 (3) was conducted, except that 1.30 g (5.00 mmol) of 2-bromo-1,1-diphenylethylene was used in place of 2-bromo-1,1-diphenylpropene. Thus, 1.03 g (57%) of the target compound was obtained as white crystals.

Melting point: 116–118° C.; $^1$H-NMR (CDCl$_3$) δ 6.85 (d, J=3.4 Hz, 1H), 7.16–7.50 (m, 20H); $^{31}$P-NMR (CDCl$_3$) δ −23.01.

EXAMPLE 8

Synthesis of 1,1-Diphenyl-2-(dicyclohexylphosphino)-3-methylbutene (Exemplified Compound 49)

(1) Synthesis of 1,1-Diphenyl-3-methylbutene

Into a reactor were introduced 2.92 g (120 mmol) of magnesium and 100 mL of THF under a nitrogen atmosphere. Iodine and bromobenzene were added to the mixture in a slight amount to ascertain initiation of a reaction. Thereafter, 17.3 g (110 mmol) of bromobenzene was gradually added dropwise thereto and the resultant mixture was refluxed for 10 minutes. Subsequently, 6.51 g (50.0 mmol) of ethyl isovalerate was gradually added dropwise to the reaction mixture while keeping the temperature of the system at about 40° C., and this mixture was refluxed for 3 hours. The resultant reaction mixture was washed with 0.1 M hydrochloric acid, saturated aqueous sodium hydrogen carbonate solution, and saturated aqueous sodium chloride solution and then dried with anhydrous magnesium sulfate. Thereafter, the solvent was removed under reduced pressure. The concentrate was dissolved in 50 mL of toluene, and 0.05 g of p-toluenesulfonic acid monohydrate was added thereto. Azeotropic dehydration was conducted for 2 hours with toluene refluxing. After being cooled, the reaction mixture was washed with saturated aqueous sodium hydrogen carbonate solution and saturated aqueous sodium chloride solution, subsequently dried with anhydrous magnesium sulfate, and then concentrated under reduced pressure to obtain 8.81 g (79%) of a transparent oily substance. $^1$H-NMR (CDCl$_3$) δ 1.01 (d, J=6.6 Hz, 6H), 2.29–2.58 (m, 1H) 5.89 (d, J=10.2 Hz, 1H), 7.13–7.43 (m, 10H)

(2) Synthesis of 2-Bromo-1,1-diphenyl-3-methylbutene

Into a reactor were introduced 8.81 g (39.6 mmol) of the 1,1-diphenyl-3-methylbutene and 35 mL of 1,2-dichloroethane under a nitrogen atmosphere. The contents were cooled to 0° C., and 6.33 g (39.6 mmol) of bromine was gradually added dropwise thereto. This mixture was stirred at room temperature for 1 hour. The resultant reaction mixture was washed with saturated aqueous sodium hydrogen carbonate solution and saturated aqueous sodium chloride solution and then dried with anhydrous magnesium sulfate. Thereafter, the solvent was removed under reduced pressure. The concentrate was recrystallized from ethanol and ethyl acetate to obtain 8.64 g (72%) of the target compound as white crystals.

Melting point: 112–114° C.; $^1$H-NMR (CDCl$_3$) δ 1.11 (d, J=6.6 Hz, 6H), 2.87 (septet, J=6.6 Hz, 1H), 7.13–7.38 (m, 10H).

(3) Synthesis of 1,1-Diphenyl-2-(dicyclohexylphosphino)-3-methylbutene (Exemplified Compound 49)

Into a reactor were introduced 1.20 g (4.00 mmol) of the 2-bromo-1,1-diphenyl-3-methylbutene and 12 mL of THF under a nitrogen atmosphere. The contents were cooled to −70° C., and 2.8 mL (4.4 mmol; 1.6 M hexane solution) of butyllithium was gradually added dropwise thereto. The resultant mixture was stirred at that temperature for 30 minutes. Thereafter, 1.1 mL (4.8 mmol) of chlorodicyclohexylphosphine was added thereto, and this mixture was stirred at that temperature for 3 hours and then heated to room temperature over 13 hours. Water was added to the reaction mixture. The organic layer was extracted with ethyl acetate, and the extract was dried with anhydrous magnesium sulfate. Thereafter, the solvent was removed under reduced pressure. The concentrate was recrystallized from ethanol and toluene to obtain 0.72 g (43%) of the target compound as white crystals.

Melting point: 162–163° C.; $^1$H-NMR (CDCl$_3$) δ 0.86–2.18 (m, 22H), 1.23 (d, J=7.0 Hz, 6H), 2.63–2.92 (m, 1H), 7.05–7.33 (m, 10H) $^{31}$p-NMR (CDCl$_3$) δ −1.46.

EXAMPLE 9

Synthesis of 1,2,2-Triphenyl-1-(dicyclohexylphosphino)ethylene (Exemplified Compound 99)

(1) Synthesis of 1,1,2-Triphenylethylene

Into a reactor was introduced 41 mL (55 mmol; 1.06 M THF solution) of benzylmagnesium chloride under a nitrogen atmosphere. The contents were cooled to 0° C. Thereafter, a solution prepared by mixing 9.11 g (50.0 mmol) of benzophenone with 18 mL of THF was gradually added dropwise thereto, and this mixture was stirred at room temperature for 1 hour. The resultant reaction mixture was washed with 0.1 M hydrochloric acid, saturated aqueous sodium hydrogen carbonate solution, and saturated aqueous sodium chloride solution and then dried with anhydrous magnesium sulfate. Thereafter, the solvent was removed under reduced pressure. The concentrate was dissolved in 46 mL of toluene, and 0.18 g of p-toluenesulfonic acid monohydrate was added thereto. Azeotropic dehydration was conducted for 2 hours with toluene refluxing. After being cooled, the reaction mixture was washed with saturated aqueous sodium hydrogen carbonate solution and saturated aqueous sodium chloride solution, subsequently dried with anhydrous magnesium sulfate, and then concentrated under reduced pressure to obtain 12.5 g (98%) of a transparent oily substance.

$^1$H-NMR (CDCl$_3$) 6.94–7.37 (m, 16H).

(2) Synthesis of 1-Bromo-1,2,2-triphenylethylene

Into a reactor were introduced 12.5 g (48.8 mmol) of the 1,1,2-triphenylethylene and 50 mL of 1,2-dichloroethane under a nitrogen atmosphere. The contents were cooled to 0° C., and 7.80 g (48.8 mmol) of bromine was gradually added dropwise thereto. This mixture was stirred at room temperature for 1 hour. The resultant reaction mixture was washed with saturated aqueous sodium hydrogen carbonate solution, saturated aqueous sodium thiosulfate solution, and saturated aqueous sodium chloride solution and then dried with anhydrous magnesium sulfate. Thereafter, the solvent was removed under reduced pressure. The resultant concentrate was recrystallized from ethanol and ethyl acetate to obtain 11.3 g (69%) of the target compound as white crystals.

Melting point: 116–118° C.; $^1$H-NMR (CDCl$_3$) δ 6.91–7.42 (m, 15H).

(3) Synthesis of 1,2,2-Triphenyl-1(dicyclohexylphosphino)ethylene (Exemplified Compound 99)

Into a reactor were introduced 1.68 g (5.0 mmol) of the 1-bromo-1,2,2-triphenylethylene, 0.134 g (5.5 mmol) of magnesium, and 13 mL of THF under a nitrogen atmosphere. Iodine and bromobenzene were added to the mixture in a slight amount to ascertain initiation of a reaction. Thereafter, the reaction mixture was refluxed for 2 hours and then cooled. Thereto were added 0.520 g (5.3 mmol) of copper chloride and 1.2 mL (5.5 mmol) of chlorodicyclohexylphosphine. This reaction mixture was refluxed for 17 hours and then cooled to room temperature. Thereto was added 17 mL of heptane. The crystals yielded were taken out by filtration and dissolved in 40 mL of ethyl acetate. The resultant solution was washed with 28% ammonia water and an aqueous sodium chloride solution and then dried with anhydrous magnesium sulfate. Thereafter, the solvent was removed under reduced pressure. The concentrate was recrystallized from ethanol to obtain 1.34 g (59%) of the target compound as white crystals.

Melting point: 121–123° C.; $^1$H-NMR (CDCl$_3$) δ 0.94–2.00 (m, 22H), 6.84–7.40 (m, 15H) $^{31}$P-NMR (CDCl$_3$) δ −0.79.

EXAMPLE 10

Synthesis of 1,1-Bis(4-methoxyphenyl)-2-(diphenylphosphino)propene (Exemplified Compound 103)

(1) Synthesis of 1,1-Bis(4-methoxyphenyl)propanol

Into a reactor were introduced 31.9 mL (30.9 mol; 0.97 M THF solution) of ethylmagnesium chloride and 20 mL of THF under a nitrogen atmosphere. The contents were cooled to 4° C. Thereafter, a solution prepared by mixing 5.00 g (20.6 mmol) of 4,4'-dimethoxybenzophenone with 20 mL of THF was gradually added dropwise thereto, and this mixture was stirred at room temperature for 1 hour. Saturated aqueous ammonium chloride solution was added to the reaction mixture. The organic layer was extracted with ethyl acetate, and the extract was dried with anhydrous magnesium sulfate and then concentrated under reduced pressure. The concentrate was purified by column chromatography to obtain 3.06 g (55%) of the target compound as a light-yellow oily substance.

$^1$H-NMR (CDCl$_3$) δ 0.86 (t, J=7.4 Hz, 3H), 1.96 (br-s, 1H), 2.22 (q, J=7.4 Hz, 2H), 3.79 (s, 6H), 6.80–6.89 (m, 4H), 7.25–7.33 (m, 4H).

(2) Synthesis of 1,1-Bis(4-methoxyphenyl)propene

Into a reactor were introduced 2.86 g (10.5 mmol) of the 1,1-bis(4-methoxyphenyl)propanol, 40 mL of toluene, and 28 mg of p-toluenesulfonic acid monohydrate under a nitrogen atmosphere. Azeotropic dehydration was conducted for 2 hours with toluene refluxing. After being cooled, the reaction mixture was washed with saturated aqueous sodium hydrogen carbonate solution and saturated aqueous sodium chloride solution, subsequently dried with anhydrous magnesium sulfate, and then concentrated under reduced pressure to obtain 2.60 g (97%) of the target compound as light-yellow crystals.

Melting point: 99–100° C.; $^1$H-NMR (CDCl$_3$) δ 1.75 (d, J=7.0 Hz, 3H), 3.79 (s, 3H), 3.84 (s, 3H), 6.03 (q, J=7.0 Hz, 1H), 6.78–6.81 (m, 2H), 6.90–6.92 (m, 2H), 7.09–7.11 (m, 2H), 7.13–7.16 (m, 2H).

(3) Synthesis of 1,1-Bis(4-methoxyphenyl)-2-bromopropene

Into a reactor were introduced 2.50 g (9.82 mmol) of the 1,1-bis(4-methoxyphenyl)propene and 25 mL of 1,2-dichloroethane under a nitrogen atmosphere. The contents were cooled to −20° C. A mixture of 1.57 g (9.82 mmol) of bromine and 13 mL of 1,2-dichloroethane was gradually added dropwise thereto, and the resultant mixture was stirred overnight at room temperature. This reaction mixture was washed with saturated aqueous sodium hydrogen carbonate solution and saturated aqueous sodium chloride solution and then dried with anhydrous magnesium sulfate. Thereafter, the solvent was removed under reduced pressure to obtain 3.26 g (100%) of the target compound as a light-yellow oily substance.

$^1$H-NMR (CDCl$_3$) δ 2.43 (s, 3H), 3.78 (s, 6H), 6.81–6.84 (m, 4H), 7.05–7.09 (m, 2H), 7.16–7.19 (m, 2H).

(4) Synthesis of 1,1-Bis(4-methoxyphenyl)-2-(diphenylphosphino)propene (Exemplified Compound 103)

Into a reactor were introduced 2.00 g (6.00 mmol) of the 1,1-bis(4-methoxyphenyl)-2-bromopropene and 30 mL of THF under a nitrogen atmosphere. The contents were cooled to −65° C., and 4.0 mL (6.0 mmol; 1.5 M hexane solution) of butyllithium was gradually added dropwise thereto. The resultant mixture was stirred for 30 minutes. Thereafter, 0.90 mL (5.0 mmol) of chlorodiphenylphosphine was added, and this mixture was stirred at that temperature for 1 hour and then at room temperature for 1 hour. Saturated aqueous ammonium chloride solution was added to the reaction mixture. The resultant mixture was extracted with ethyl acetate, and the extract was dried with anhydrous magnesium sulfate. Thereafter, the solvent was removed under reduced pressure. The concentrate was recrystallized from ethanol to obtain 1.45 g (66%) of the target compound as white crystals.

Melting point: 123–125° C.; $^1$H-NMR (CDCl$_3$) δ 1.71 (d, J 2.9 Hz, 3H), 3.76 (s, 3H), 3.79 (s, 3H), 6.74–6.77 (m, 2H), 6.82–6.85 (m, 2H), 7.05–7.10 (m, 4H), 7.32–7.40 (m, 10H); $^{31}$P-NMR (CDCl$_3$) δ −3.73.

EXAMPLE 11

Synthesis of 1,1-Bis(4-fluorophenyl)-2-(diphenylphosphino)propene (Exemplified Compound 107)

(1) Synthesis of 1,1-Bis(4-fluorophenyl)propanol

Into a reactor were introduced 10.0 g (40.6 mmol) of cerium chloride and 80 mL of THF under a nitrogen atmosphere. This mixture was stirred at room temperature for 20 hours and then cooled to 0° C. Thereto was added dropwise 25.1 mL (24.3 mmol; 0.97 M THF solution) of ethylmagnesium chloride over 30 minutes. Subsequently, a solution prepared by mixing 3.54 g (16.2 mmol) of 4,4'-difluorobenzophenone with 20 mL of THF was added dropwise thereto over 40 minutes, and this mixture was stirred for 1 hour. To the resultant reaction mixture was added 10% aqueous acetic acid solution. Thereafter, the mixture was extracted with ethyl acetate, and the resultant organic layer was washed with saturated aqueous sodium hydrogen carbonate solution and saturated aqueous sodium chloride solution, subsequently dried with anhydrous magnesium sulfate, and then concentrated under reduced pressure. The concentrate was purified by column chromatography to obtain 3.12 g (78%) of the target compound as a light-yellow oily substance.

$^1$H-NMR (CDCl$_3$) δ 0.85 (t, J=7.4 Hz, 3H), 2.05 (s, 1H) 2.26 (q, J=7.4 Hz, 2H), 6.95–7.00 (m, 4H), 7.32–7.37 (m, 4H).

(2) Synthesis of 1,1-Bis(4-fluorophenyl)propene

Into a reactor were introduced 2.80 g (11.3 mmol) of the 1,1-bis(4-fluorophenyl)propanol, 60 mL of toluene, and 14 mg of p-toluenesulfonic acid monohydrate under a nitrogen atmosphere. Azeotropic dehydration was conducted for 1 hour with toluene refluxing. After being cooled, the reaction mixture was washed with saturated aqueous sodium hydrogen carbonate solution and saturated aqueous sodium chloride solution, subsequently dried with anhydrous magnesium sulfate, and then concentrated under reduced pressure to obtain 2.39 g (92%) of the target compound as white crystals.

Melting point: 43–44° C.; $^1$H-NMR (CDCl$_3$) δ 1.74 (d, J=7.0 Hz, 3H), 6.09 (q, J=7.0 Hz, 1H), 6.91–6.96 (m, 2H), 7.04–7.08 (m, 2H), 7.10–7.17 (m, 4H).;

(3) Synthesis of 1,1-Bis(4-fluorophenyl)-2-bromopropene

Into a reactor were introduced 2.00 g (8.69 mmol) of the 1,1-bis(4-fluorophenyl)propene and 25 mL of 1,2-dichloroethane under a nitrogen atmosphere. The contents were cooled to −20° C. A mixture of 1.39 g (8.69 mmol) of bromine and 12 mL of 1,2-dichloroethane was added dropwise thereto over 1 hour, and the resultant mixture was stirred at that temperature for 1 hour and then at room temperature for 16 hours. Subsequently, a solution prepared by mixing 0.703 mL (8.69 mmol) of pyridine with 20 mL of toluene was added dropwise thereto over 15 minutes, and this mixture was stirred at 100° C. for 2 hours and then cooled. Saturated aqueous sodium hydrogen carbonate solution was added to the resultant reaction mixture, which was then extracted with toluene. The resultant organic layer was washed with saturated aqueous sodium chloride solution and then dried with anhydrous magnesium sulfate. Thereafter, the solvent was removed under reduced pressure. The concentrate was recrystallized from ethanol to obtain 1.21 g (45%) of the target compound as white crystals.

Melting point: 53–54° C.; $^1$H-NMR (CDCl$_3$) δ 2.42 (s, 3H), 6.98–7.03 (m, 4H), 7.11–7.13 (m, 2H), 7.19–7.23 (m, 2H)

(4) Synthesis of 1,1-Bis (4-fluorophenyl)-2-(diphenylphosphino)propene (Exemplified Compound 107)

Into a reactor were introduced 0.907 g (2.93 mmol) of the 1,1-bis(4-fluorophenyl)-2-bromopropene and 20 mL of THF under a nitrogen atmosphere. The contents were cooled to −65° C., and 2.0 mL (2.9 mmol; 1.5 M hexane solution) of butyllithium was gradually added dropwise thereto. The resultant mixture was stirred for 40 minutes. Thereafter, a mixture of 0.58 mL (3.2 mmol) of chlorodiphenylphosphine and 5 mL of THF was added thereto, and the resultant mixture was stirred at that temperature for 2 hours and then heated to room temperature. Saturated aqueous ammonium chloride solution was added to the reaction mixture, which was then extracted with ethyl acetate. The resultant organic layer was washed with water and saturated aqueous sodium chloride solution and then dried with anhydrous magnesium sulfate. Thereafter, the solvent was removed under reduced pressure. The concentrate was recrystallized from methanol to obtain 0.687 g (57%) of the target compound as white crystals.

Melting point: 88–90° C.; $^1$H-NMR (CDCl$_3$) δ 1.63 (d, J=2.8 Hz, 3H), 6.81–6.87 (m, 2H), 6.90–6.96 (m, 2H), 7.00–7.08 (m, 4H), 7.25–7.32 (m, 10H); $^{31}$P-NMR (CDCl$_3$) δ −4.40; $^{19}$F-NMR (CDCl$_3$) δ −−115.0, −114.9.

EXAMPLE 12

Into a reactor were introduced 0.85 g (5.0 mmol) of diphenylamine and 0.76 g of o-terphenyl as an internal standard substance under a nitrogen atmosphere. Thereto was added 10 mL of toluene to dissolve those ingredients. To this solution were added 0.53 g (5.5 mmol) of sodium t-butoxide, 0.95 mL (5.5 mmol) of 1-bromo-4-tert-butylbenzene, 2.8 mg (0.25 mol % based on the amine) of palladium acetate, and 23.2 mg (1.0 mol % based on the amine) of the 1,1-bis(4-dimethylaminophenyl)-2-(diphenylphosphino)propene obtained in Example 4. This mixture was stirred at 100° C. for 8 hours and then cooled. The resultant reaction mixture was analyzed by gas chromatography to determine the amount of diphenyl(4-tert-butylphenyl)amine as the target compound by the internal-standard determination method. The results obtained are shown in Table 18.

H-NMR (CDCl$_3$) δ 1.31 (s, 9H), 6.92–7.30 (m, 14H).

EXAMPLE 13

The same procedure as in Example 12 was conducted, except that the palladium compound was replaced with 2.3 mg (0.25 mol % based on the amine) of (π-allyl)palladium chloride. The amount of diphenyl(4-tert-butylphenyl)amine as the target compound was determined by the internal-standard determination method by gas chromatography. The results obtained are shown in Table 18.

EXAMPLE 14

The same procedure as in Example 12 was conducted, except that the palladium compound was replaced with 4.8 mg (0.25 mol % based on the amine) of dichlorobis (benzonitrile)palladium. The amount of diphenyl(4-tert-butylphenyl)amine as the target compound was determined by the internal-standard determination method by gas chromatography. The results obtained are shown in Table 18.

EXAMPLE 15

The same procedure as in Example 12 was conducted, except that the palladium compound was replaced with 3.8 mg (0.25 mol % based on the amine) of palladium acetylacetonate. The amount of diphenyl(4-tert-butylphenyl) amine as the target compound was determined by the internal-standard determination method by gas chromatography. The results obtained are shown in Table 18.

EXAMPLE 16

The same procedure as in Example 12 was conducted, except that the palladium compound was replaced with 14.4 mg (0.25 mol % based on the amine) of tetrakis (triphenylphosphine)palladium. The amount of diphenyl(4-tert-butylphenyl)amine as the target compound was determined by the internal-standard determination method by gas chromatography. The results obtained are shown in Table 18.

EXAMPLE 17

The same procedure as in Example 12 was conducted, except that the palladium compound was replaced with 5.7 mg (0.25 mol % based on the amine) of tris (dibenzylideneacetone)dipalladium. The amount of diphenyl(4-tert-butylphenyl)amine as the target compound was determined by the internal-standard determination method by gas chromatography. The results obtained are shown in Table 18.

| Example | Palladium | Yield (%) |
| --- | --- | --- |
| Example 12 | Pd (OAc)$_2$ | 85 |
| Example 13 | [(n-allyl)PdCl]$_2$ | 83 |
| Example 14 | (C$_6$H$_5$CN)$_2$PdCl$_2$ | 86 |
| Example 15 | Pd (acac)$_2$ | 78 |
| Example 16 | Pd (PPh$_3$)$_4$ | 83 |
| Example 17 | Pd$_2$ (dba)$_3$ | 78 |

EXAMPLE 18

The same procedure as in Example 12 was conducted, except that the phosphine was replaced with 20.7 mg (1.0 mol % based on the amine) of the 1,1-bis(4-dimethylaminophenyl)-2-(diphenylphosphino)propene obtained in Example 4. The amount of diphenyl(4-tert-butylphenyl)amine as the target compound was determined by the internal-standard determination method by gas chromatography. The results obtained are shown in Table 19.

EXAMPLE 19

The same procedure as in Example 12 was conducted, except that the phosphine was replaced with 18.9 mg (1.0 mol % based on the amine) of the 1,1-diphenyl-2-(diphenylphosphino)propene obtained in Example 1. The amount of diphenyl(4-tert-butylphenyl)amine as the target compound was determined by the internal-standard determination method by gas chromatography. The results obtained are shown in Table 19.

EXAMPLE 20

The same procedure as in Example 12 was conducted, except that the phosphine was replaced with 19.5 mg (1.0 mol % based on the amine) of the 1,1-diphenyl-2-(dicyclohexylphosphino)propene obtained in Example 2 and that the reaction time was changed to 3 hours. The amount of diphenyl(4-tert-butylphenyl)amine as the target compound was determined by the internal-standard determination method by gas chromatography. The results obtained are shown in Table 19.

EXAMPLE 21

The same procedure as in Example 12 was conducted, except that the phosphine and palladium acetate were replaced with 19.5 mg (1.0 mol % based on the amine) of the 1,1-diphenyl-2-(di-t-butylphosphino)propene obtained in Example 3 and 2.3 mg (1.0 mol % based on the amine) of (π-allyl)palladium chloride, respectively, and that the reaction time was changed to 3 hours. The amount of diphenyl(4-tert-butylphenyl)amine as the target compound was determined by the internal-standard determination method by gas chromatography. The results obtained are shown in Table 19.

EXAMPLE 22

The same procedure as in Example 12 was conducted, except that the phosphine was replaced with 18.2 mg (1.0 mol % based on the amine) of the 2,2-diphenyl-1-(diphenylphosphino)ethylene obtained in Example 7. The amount of diphenyl(4-tert-butylphenyl)amine as the target compound was determined by the internal-standard determination method by gas chromatography. The results obtained are shown in Table 19.

EXAMPLE 23

The same procedure as in Example 12 was conducted, except that the phosphine was replaced with 23.8 mg (1.0 mol % based on the amine) of the 1,1-bis(4-dimethylaminophenyl)-2-(dicyclohexylphosphino)propene obtained in Example 5 and that the reaction time was changed to 3 hours. The amount of diphenyl(4-tert-butylphenyl)amine as the target compound was determined by the internal-standard determination method by gas chromatography. The results obtained are shown in Table 19.

EXAMPLE 24

The same procedure as in Example 12 was conducted, except that the phosphine was replaced with 21.2 mg (1.0 mol % based on the amine) of the 1,1-bis(4-dimethylaminophenyl)-2-(di-t-butylphosphino)propene obtained in Example 6. The amount of diphenyl(4-tert-butylphenyl)amine as the target compound was determined by the internal-standard determination method by gas chromatography. The results obtained are shown in Table 19.

EXAMPLE 25

The same procedure as in Example 12 was conducted, except that the phosphine was replaced with 20.9 mg (1.0 mol % based on the amine) of the 1,1-diphenyl-2-(dicyclohexylphosphino)-3-methylbutene obtained in Example 8. The amount of diphenyl(4-tert-butylphenyl)amine as the target compound was determined by the internal-standard determination method by gas chromatography. The results obtained are shown in Table 19.

EXAMPLE 26

The same procedure as in Example 12 was conducted, except that the phosphine was replaced with 22.6 mg (1.0 mol % based on the amine) of the 1,2,2-triphenyl-1-(dicyclohexylphosphino)ethylene obtained in Example 9. The amount of diphenyl(4-tert-butylphenyl)amine as the target compound was determined by the internal-standard determination method by gas chromatography. The results obtained are shown in Table 19.

COMPARATIVE EXAMPLE 1

The same procedure as in Example 12 was conducted, except that the phosphine was replaced with 13.1 mg (1.0 mol % based on the amine) of triphenylphosphine. The amount of diphenyl(4-tert-butylphenyl)amine as the target compound was determined by the internal-standard determination method by gas chromatography. The results obtained are shown in Table 19.

COMPARATIVE EXAMPLE 2

The same procedure as in Example 12 was conducted, except that the phosphine was replaced with 15.2 mg (1.0 mol % based on the amine) of tris(o-tolyl)phosphine. The amount of diphenyl(4-tert-butylphenyl)amine as the target compound was determined by the internal-standard determination method by gas chromatography. The results obtained are shown in Table 19.

COMPARATIVE EXAMPLE 3

The same procedure as in Example 12 was conducted, except that the phosphine was replaced with 11.7 mg (1.0 mol % based on the amine) of BINAP (2,2-bis(diphenylphosphino)-1,1'-binaphthyl). The amount of diphenyl(4-tert-butylphenyl)amine as the target compound was determined by the internal-standard determination method by gas chromatography. The results obtained are shown in Table 19.

COMPARATIVE EXAMPLE 4

The same procedure as in Example 12 was conducted, except that the phosphine was replaced with 14.0 mg (1.0 mol % based on the amine) of triscyclohexylphosphine. The amount of diphenyl(4-tert-butylphenyl)amine as the target compound was determined by the internal-standard determination method by gas chromatography. The results obtained are shown in Table 19.

COMPARATIVE EXAMPLE 5

The same procedure as in Example 12 was conducted, except that the phosphine was replaced with 10.6 mg (1.0 mol % based on the amine) of vinyldiphenylphosphine. The amount of diphenyl(4-tert-butylphenyl)amine as the target compound was determined by the internal-standard determination method by gas chromatography. The results obtained are shown in Table 19.

TABLE 19

| | Phosphine | Time (hr) | Yield % |
|---|---|---|---|
| Example 18 | (4-Me$_2$N—C$_6$H$_4$)$_2$C=C (Me) PPh$_2$ | 8 | 85 |
| Example 19 | Ph$_2$C=C (Me) PPh$_2$ | 8 | 88 |
| Example 20 | Ph$_2$C=C (Me) PCy$_2$ | 3 | 96 |
| Example 21 | Ph$_2$C=C (Me) P—tBu$_2$ | 3 | 89 |
| Example 22 | Ph$_2$C=C (H) PPh$_2$ | 8 | 45 |
| Example 23 | (4-Me$_2$N—C$_6$H$_4$)$_2$C=C (Me) PCy$_2$ | 3 | 87 |
| Example 24 | (4-Me$_2$N—C$_6$H$_4$)$_2$C=C (Me) P—tBu$_2$ | 8 | 88 |
| Example 25 | Ph$_2$C=C (iPr) PCy$_2$ | 8 | 45 |
| Example 26 | Ph$_2$C=C (Ph) PCy$_2$ | 8 | 40 |
| Comparative Example 1 | Ph$_3$P | 8 | 10 |
| Comparative Example 2 | (o-tolyl)$_3$P | 8 | 30 |
| Comparative Example 3 | BINAP | 8 | 22 |
| Comparative Example 4 | Cy$_3$P | 8 | 37 |
| Comparative Example 5 | Vinyl-PPh$_2$ | 8 | 1 |

Table 19 shows that when the 2,2-(diaryl)vinylphosphine compounds according to the invention (Examples 18 to 26) were used to conduct an amination reaction, the target arylamine could be obtained in high yield. In contrast, when triphenylphosphine (Comparative Example 1), tris(o-tolyl)phosphine (Comparative Example 2), BINAP (Comparative Example 3), triscyclohexylphosphine (Comparative Example 4), and vinyldiphenylphosphine (Comparative Example 5) were used as phosphines in place of the 2,2-(diaryl)vinylphosphine compounds of the invention to conduct the reaction, the yield of the target arylamine was as low as 37% at the most.

As demonstrated above, those 2,2-(diaryl)vinylphosphine compounds according the invention are exceedingly useful phosphines in completing the amination reaction of the invention.

EXAMPLE 27

Synthesis of N-p-Methoxyphenyl-N-p-tolylamine

Into a reactor were introduced 0.214 g (2.00 mmol) of p-toluidine and 4 mL of dioxane under a nitrogen atmosphere. The amine was dissolved in the solvent. To this solution were added 0.515 g (2.2 mol) of p-iodoanisole, 0.231 g (2.4 mmol) of sodium t-butoxide, 4.5 mg (1 mol % based on the amine) of palladium acetate, and 15.6 mg (2 mmol % based on the amine) of the 1,1-diphenyl-2-(dicyclohexylphosphino)propene obtained in Example 2. The resultant reaction mixture was stirred at 100° C. for 8 hours and then cooled. Saturated aqueous ammonium chloride solution was added thereto, and this mixture was extracted with toluene. The extract was dried with anhydrous magnesium sulfate. Thereafter, the solvent was removed under reduced pressure. The concentrate was purified by column chromatography to obtain 0.351 g (82%) of N-p-methoxyphenyl-N-p-tolylamine as yellow crystals. The results obtained are shown in Table 20.

Melting point: 81–82° C.; $^1$H-NMR (CDCl$_3$) δ 2.74 (s, 3H), 3.79 (s, 3H), 5.38 (br-s, 1H), 6.78–6.91 (m, 4H), 6.96–7.09 (m, 4H).

EXAMPLE 28

Synthesis of N-p-Methoxyphenyl-N-p-tolylamine

Into a reactor were introduced 0.330 g (1.93 mmol) of p-tolyl bromide and 4 mL of toluene under a nitrogen atmosphere. The bromide was dissolved in the solvent. To this solution were added 0.266 g (2.16 mmol) of p-anisidine, 0.226 g (2.35 mmol) of sodium t-butoxide, 8.5 mg (1 mol % based on the amine) of tris(dibenzylidene)dipalladium, and 32.3 mg (2 mmol % based on the amine) of the 1,1-diphenyl-2-(dicyclohexylphosphino)propene obtained in Example 2. The resultant reaction mixture was stirred at 100° C. for 5 hours and then cooled. Saturated aqueous ammonium chloride solution was added thereto, and this mixture was extracted with toluene. The extract was dried with anhydrous magnesium sulfate. Thereafter, the solvent was removed under reduced pressure. The concentrate was purified by column chromatography to obtain 0.366 g (89%) of N-p-methoxyphenyl-N-p-tolylamine. The results obtained are shown in Table 20.

EXAMPLE 29

Synthesis of N-(Diphenylmethylene)-4-aminobiphenyl

Into a reactor were introduced 0.466 g (2.00 mmol) of 4-bromobiphenyl and 4 mL of toluene under a nitrogen atmosphere. The bromobiphenyl was dissolved in the solvent. To this solution were added 0.399 g (2.2 mmol) of benzophenonimine, 0.231 g (2.4 mmol) of sodium t-butoxide, 13.5 mg (3 mol % based on the amine) of palladium acetate, and 46.9 mg (6 mmol % based on the amine) of the 1,1-diphenyl-2-(dicyclohexylphosphino)propene obtained in Example 2. The resultant reaction mixture was stirred at 100° C. for 16 hours and then cooled. Saturated aqueous ammonium chloride solution was added thereto, and this mixture was extracted with toluene. The extract was dried with anhydrous magnesium sulfate. Thereafter, the solvent was removed under reduced pressure. The concentrate was purified by column chromatography to obtain 0.409 g (61%) of N-(diphenylmethylene)-4-aminobiphenyl as a yellow oily substance. The results obtained are shown in Table 20.

$^1$H-NMR (CDCl$_3$) 6.74–7.88 (m, 19H)

EXAMPLE 30

Synthesis of N-(4-Cyanophenyl)morpholine

Into a reactor were introduced 0.275 g (2.00 mmol) of 4-chlorobenzonitrile and 4 mL of toluene under a nitrogen atmosphere. The nitrile was dissolved in the solvent. To this solution were added 0.192 g (2.2 mmol) of morpholine, 0.231 g (2.4 mmol) of sodium t-butoxide, 4.5 mg (1 mol % based on the amine) of palladium acetate, and 15.6 mg (2 mmol % based on the amine) of the 1,1-diphenyl-2 (dicyclohexylphosphino)propene obtained in Example 2. The resultant reaction mixture was stirred at 100° C. for 14 hours and then cooled. Saturated aqueous ammonium chloride solution was added thereto, and this mixture was extracted with toluene. The extract was dried with anhydrous magnesium sulfate. Thereafter, the solvent was removed under reduced pressure. The concentrate was purified by column chromatography to obtain 0.304 g (81%) of N-(4-cyanophenyl)morpholine as light-yellow crystals. The results obtained are shown in Table 20.

Melting point: 80–81° C.; $^1$H-NMR (CDCl$_3$) δ 3.23–3.33 (m, 4H), 3.80–3.90 (m, 4H), 6.81–6.92 (m, 2H), 7.47–7.57 (m, 2H)

EXAMPLE 31

Synthesis of Ditolylamine

Into a reactor were introduced 0.503 g (2.10 mmol) of p-tolyl triflate and 4 mL of dioxane under a nitrogen atmosphere. The triflate was dissolved in the solvent. To this solution were added 0.246 g (2.29 mmol) of p-toluidine, 0.658 g (3.10 mmol) of potassium phosphate, 19.9 mg (2.1 mol % based on the triflate) of tris(dibenzylideneacetone) dipalladium, and 58.7 mg (7.2 mmol % based on the triflate) of the 1,1-diphenyl-2(dicyclohexylphosphino)propene obtained in Example 2. The resultant reaction mixture was stirred at 100° C. for 12 hours and then cooled. Saturated aqueous ammonium chloride solution was added thereto, and this mixture was extracted with toluene. The extract was dried with anhydrous magnesium sulfate. Thereafter, the solvent was removed under reduced pressure. The concentrate was purified by column chromatography to obtain 0.268 g (65%) of ditolylamine. The results obtained are shown in Table 20.

Melting point: 78–82° C.; $^1$H-NMR (CDCl$_3$) δ 2.32 (s, 6H), 5.51 (br-s, 1H), 6.88–7.17 (m, 8H).

EXAMPLE 32

Synthesis of N-(3-Thiophenyl)-N,N-diphenylamine

Into a reactor were introduced 0.358 g (2.20 mmol) of 3-bromothiophene and 4 mL of toluene under a nitrogen atmosphere. The bromothiophene was dissolved in the solvent. To this solution were added 0.343 g (2.03 mmol) of diphenylamine, 0.229 g (2.39 mmol) of sodium t-butoxide, 4.4 mg (1 mol % based on the amine) of palladium acetate, and 30.6 mg (2 mmol % based on the amine) of the 1,1-diphenyl-2-(dicyclohexylphosphino)propene obtained in Example 2. The resultant reaction mixture was stirred at 100° C. for 10 hours and then cooled. Saturated aqueous ammonium chloride solution was added thereto, and this mixture was extracted with toluene. The extract was dried with anhydrous magnesium sulfate. Thereafter, the solvent was removed under reduced pressure. The concentrate was purified by column chromatography to obtain 0.257 g (50%) of N-(3-thiophenyl)-N,N-diphenylamine. The results obtained are shown in Table 20.

Melting point: 79–82° C.; $^1$H-NMR (CDCl$_3$) δ 6.66 (d/d, J=1.4, 3.1 Hz, 1H), 6.88 (d/d, J=1.4, 5.1 Hz, 1H), 6.94–7.36 (m,11H).

COMPARATIVE EXAMPLE 6

Synthesis of N-p-Methoxyphenyl-N-p-tolylamine

The same procedure as in Example 27 was conducted, except that the phosphine was replaced with 4.2 mg (1.0 mol % based on the amine) of vinyldiphenylphosphine. The amount of N-p-methoxyphenyl-N-p-tolylamine as the target compound was determined by the internal-standard determination method by gas chromatography. As a result, the yield was found to be 5%. The results obtained are shown in Table 20.

COMPARATIVE EXAMPLE 7

Synthesis of N-p-Methoxyphenyl-N-p-tolylamine

The same procedure as in Example 28 was conducted, except that the phosphine was replaced with 4.2 mg (1.0 mol % based on the amine) of vinyldiphenylphosphine. The amount of N-p-methoxyphenyl-N-p-tolylamine as the target compound was determined by the internal-standard determination method by gas chromatography. As a result, the yield was found to be 5%. The results obtained are shown in Table 20.

TABLE 20

| Example | Aryl compound | Amine | Product | Yield (%) |
| --- | --- | --- | --- | --- |
| Example 27 | MeO—⟨⟩—I | —⟨⟩—NH$_2$ | MeO—⟨⟩—NH—⟨⟩— | 82 |
| Comparative Example 6 | MeO—⟨⟩—I | —⟨⟩—NH$_2$ | MeO—⟨⟩—NH—⟨⟩— | 5 |
| Example 28 | —⟨⟩—Br | MeO—⟨⟩—NH$_2$ | MeO—⟨⟩—NH—⟨⟩— | 89 |
| Comparative Example 7 | —⟨⟩—Br | MeO—⟨⟩—NH$_2$ | MeO—⟨⟩—NH—⟨⟩— | 5 |
| Example 29 | ⟨⟩—⟨⟩—Br | Ph$_2$C=NH | Ph$_2$C=N—⟨⟩—⟨⟩ | 61 |

TABLE 20-continued

| Example | Aryl compound | Amine | Product | Yield (%) |
|---|---|---|---|---|
| Example 30 | Cl–⟨C6H4⟩–CN | O⟨morpholine⟩NH | O⟨morpholine⟩N–⟨C6H4⟩–CN | 81 |
| Example 31 | MeO–⟨C6H4⟩–OTf | ⟨C6H4-Me⟩–NH2 | ⟨C6H4-OMe⟩–NH–⟨C6H4-Me⟩ | 65 |
| Example 32 | 3-bromothiophene | Ph–NH–Ph | Ph2N–(3-thienyl) | 50 |

Table 20 shows that when the 2,2-(diaryl)vinylphosphine compound according to the invention (Examples 27 to 32) was used to conduct amination reactions, the target arylamines could be obtained in high yields. In contrast, when vinyldiphenylphosphine (Comparative Examples 6 and 7) was used as a phosphine in place of the 2,2-(diaryl) vinylphosphine compound of the invention to conduct amination reactions, the yield of the target arylamines was as low as 5%.

As demonstrated above, that 2,2-(diaryl)vinylphosphine compound according the invention is an exceedingly useful phosphine in completing the amination reaction of the invention.

EXAMPLE 33

Synthesis of [1,1-Diphenyl-2-(di-tert-butylphosphino)propene] (π-allyl)palladium Chloride Into a reactor were introduced 0.183 g (0.5 mmol) of (π-allyl)palladium chloride dimer, 0.338 g (1.0 mmol) of the 1,1-diphenyl-2-(di-t-butylphosphino)propene obtained in Example 3, and 3 mL of toluene under a nitrogen atmosphere. The contents were stirred at room temperature for 62 hours. To the resultant reaction mixture was added 3 mL of heptane. This mixture was stirred for 30 minutes. The crystals yielded were taken out by filtration and dried to obtain 0.25 g (48%) of the target compound.

$^{31}$P-NMR (CDCl$_3$) δ 63.83; MS (EI): 519, 521.

EXAMPLE 34

The same procedure as in Example 12 was conducted, except that the palladium compound and phosphine were replaced with the [1,1-diphenyl-2-(di-tert-butylphosphino) propene] (π-allyl)palladium chloride (palladium-phosphine catalyst) obtained in Example 33. The amount of diphenyl (4-tert-butylphenyl)amine as the target compound was determined by the internal-standard determination method by gas chromatography. As a result, the yield of the target compound was 90%.

Example 35

Synthesis of 4-Methylbiphenyl

Into a reactor were introduced 0.123 ml (1.0 mmol) of 1-bromotoluene, 0.1829 g (1.5 mmol) of phenylboric acid, 87.2 mg (1.5 mmol) of potassium fluoride, 4.5 mg (0.02 mmol) of palladium acetate, 11.7 mg (0.03 mmol) of the 1,1-diphenyl-2-(dicyclohexylphosphine)propene obtained in Example 2, and 3.0 ml of dioxane under a nitrogen atmosphere. The resultant reaction mixture was stirred at room temperature for 20 hours. The amount of 4-methylbiphenyl as the target compound was determined by the internal-standard determination method by gas chromatography. As a result, the yield was found to be 70%.

$^1$H-NMR (CDCl$_3$) δ 2.39 (s, 3H), 7.19–7,65 (m, 9H).

Example 36

Synthesis of 4-Methylbiphenyl

Into a reactor were introduced 0.123 ml (1.0 mmol) of 1-bromotoluene, 0.1829 g (1.5 mmol) of phenylboric acid, 87.2 mg (1.5 mmol) of potassium fluoride, 4.5 mg (0.02 mmol) of palladium acetate, 11.7 mg (0.03 mmol) of the 1,1-diphenyl-2-(dicyclohexylphosphine)propene obtained in Example 2, and 3.0 ml of dioxane under a nitrogen atmosphere. The resultant reaction mixture was stirred at 80° C. for 4 hours. The amount of 4-methylbiphenyl as the target compound was determined by the internal-standard determination method by gas chromatography. As a result, the yield was found to be 95%.

Example 37

Synthesis of 2-Phenylpyridine

Into a reactor were introduced 0.79 g (5.0 mmol) of 2-bromo-pyridine, 0.73 g (6.0 mmol) of phenylboric acid, 1.38 g (10.0 mmol) of potassium carbonate, 11.2 mg (0.05 mmol) of palladium acetate, 39.1 mg (0.1 mmol) of the 1,1-diphenyl-2-(dicyclohexylphosphine)propene obtained in Example 2, 5.0 ml of water, and 15.0 ml of toluene under a nitrogen atmosphere. The resultant reaction mixture was stirred at 80° C. for 4 hours and then cooled. Thereafter, the solvent was removed under pressure. The concentrate was purified by column clromatography to obtain 0.66 g (85%) of 2-phenylpyridine as the target compound.

$^1$H-NMR (CDCl$_3$) δ 7.15–7.29 (m, 1H), 7.34–7.55 (m, 3H), 7.68–7.80 (m, 2H), 7.92–8.04 (m, 2H), 8.65–8.74 (m, 1H).

Example 38

Synthesis of 4-(4-Cyanophenyl)-2-methyl-3-butyne-2-ol

Into a reactor were introduced 1.38 g (10.0 mmol) of 4-chlorobenzonitrile, 1.68 g (20.0 mmol) of 2-methyl-3 butyne-2-ol, 2.7 mg (0.015 mmol) of palladium, 1.4 mg (0.0075 mmol) of copper iodide, 17.6 mg (0.045 mmol) of the 1,1-diphenyl-2-(dicyclohexylphosphine)propene obtained in Example 2, 4.0 mL (0.055 mmol) of diisopropylamine, and 4.0 ml of N,N-dimethylformamide under a nitrogen atmosphere. The resultant reaction mixture was stirred at 100° C. for 23 hours and then cooled. Thereafter, the solvent was removed under pressure. The concentrate was purified by column clromatography to obtain 1.56 g (84%) of 4-(4-cyanophenyl)-2-methyl-3-butyne-2-ol as white crystals.

$^1$H-NMR (CDCl$_3$) δ 1.63 (s, 6H), 2.23 (br-s, 1H), 7.44–7.65 (m. 4H)

While the invention has been described in detail and with reference to specific embodiments thereof, it will be apparent to one skilled in the art that various changes and modifications can be made therein without departing from the spirit and scope thereof.

This application is based on Japanese patent application No. 2000-194690 filed on Jun. 28, 2000, the entire contents thereof being hereby incorporated by reference.

What is claimed is:

1. A 2,2-(diaryl)vinylphosphine compound represented by formula (1):

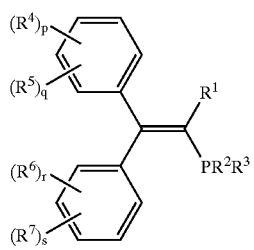

wherein $R^1$ is an alkyl group having 1 to 6 carbon atoms, an alicyclic group having 5 to 7 carbon atoms, or a phenyl group which may have one or more substituents;

$R^2$ and $R^3$ are independently an alkyl group having 1 to 6 carbon atoms, an alicyclic group having 5 to 7 carbon atoms, or a phenyl group which may have one or more substituents;

$R^4$, $R^5$, $R^6$, and $R^7$ are independently an alkyl group having 1 to 6 carbon atoms, an alicyclic group having 5 to 7 carbon atoms, a phenyl group which may have one or more substituents, an alkoxy group having 1 to 6 carbon atoms, a dialkylamino group in which each alkyl has 1 to 3 carbon atoms, a halogen atom, a benzyl group, a naphthyl group, or a halogen-substituted lower alkyl group having 1 or 2 carbon atoms, provided that $R^4$ and $R^5$ taken together and/or $R^6$ and $R^7$ taken together may represent a fused benzene ring, a substituted fused benzene ring, a trimethylene group, a tetramethylene group, or a methylenedioxy group; and p, q, r, and s are independently 0 to 5, provided that p+q and r+s each is in the range of from 0 to 5.

2. A palladium-phosphine catalyst obtained by reacting a palladium compound with the 2,2-(diaryl)vinylphosphine compound of claim 1.

3. The palladium-phosphine catalyst of claim 2, wherein the palladium compound is a salt or complex of palladium having a valence of 4, 2, or 0.

4. A process for producing an arylamine compound which comprises the steps of:

selecting the palladium-phosphine catalyst of claim 2 or 3;

selecting an aryl compound represented by formula (2):

$$ArX^1 \qquad (2)$$

wherein Ar is an aryl group which may have one or more substituents, or a heteroaryl group which may have one or more substituents; and $X^1$ is a halogen atom, a trifluoromethanesulfonyloxy group, a methanesulfonyloxy group, or a toluenesulfonyloxy group; and utilizing said aryl compound to conduct an animation reaction with an amine compound in the presence of a base and said palladium-phosphine catalyst to produce said arylamine compound.

5. A process for producing a diaryl compound which comprises the steps of:

selecting the palladium-phosphine catalyst of claim 2 or 3;

selecting an aryl compound represented by formula (2)

$$ArX^1 \qquad (2)$$

wherein Ar is an aryl group which may have one or more substituents, or a heteroaryl group which may have one or more substituents; and $X^1$ is a halogen atom, a trifluoromethanesulfonyloxy group, a methanesulfonyloxy group, or a toluenesulfonyloxy group; and utilizing said aryl compound to conduct carbon-carbon bond formation with an arylboric acid compound or an arylborate ester compound in the presence of a base and said palladium-phosphine catalyst to produce said diaryl compound.

6. A process for producing an arylalkyne compound which comprises the steps of:

selecting the palladium-phosphine catalyst of claim 2 or 3;

selecting an aryl compound represented by formula (2)

$$ArX^1 \qquad (2)$$

wherein Ar is an aryl group which may have one or more substituents, or a heteroaryl group which may have one or more substituents; and $X^1$ is a halogen atom, a trifluoromethanesulfonyloxy group, a methanesulfonyloxy group, or a toluenesulfonyloxy group; and utilizing said aryl compound to conduct carbon-carbon bond formation with an alkyne compound in the presence of a base and said palladium-phosphine catalyst to produce said arylalkyne compound.

7. The 2,2-(diaryl) phosphine compound according to claim 1 wherein $R^1$ is methyl, ethyl, propyl or butyl.

8. The 2,2-(diaryl) phosphine compound according to claim 7 wherein $R^2$ and $R^3$ are methyl.

9. The 2,2-(diaryl) phosphine compound according to claim 7 wherein $R^2$ and $R^3$ are ethyl.

10. The 2,2-(diaryl) phosphine compound according to claim 7 wherein $R^2$ and $R^3$ are propyl.

11. The 2,2-(diaryl) phosphine compound according to claim 7 wherein $R^2$ and $R^3$ are butyl.

12. The 2,2-(diaryl) phosphine compound according to claim 7 wherein $R^2$ and $R^3$ are independently cyclopentyl, cyclohexyl or phenyl.

13. The 2,2-(diaryl) phosphine compound according to claim 1 wherein $R^1$ is cyclohexyl or phenyl.

14. The 2,2-(diaryl) phosphine compound according to claim 13 wherein $R^2$ and $R^3$ are methyl.

15. The 2,2-(diaryl) phosphine compound according to claim 13 wherein $R^2$ and $R^3$ are ethyl.

16. The 2,2-(diaryl) phosphine compound according to claim 13 wherein $R^2$ and $R^3$ are propyl.

17. The 2,2-(diaryl) phosphine compound according to claim 13 wherein $R^2$ and $R^3$ are butyl.

18. The 2,2-(diaryl) phosphine compound according to claim 13 wherein $R^2$ and $R^3$ are independently cyclopentyl, cyclohexyl or phenyl.

19. The 2,2-(diaryl) phosphine compound according to any of claims 7–18, wherein $R^4$, $R^5$, $R^6$ and $R^7$ are independently selected from the group consisting of methyl, ethyl, methoxy, ethoxy, dimethylamino, diethylamino, fluoro, chloro, bromo, phenyl and butyl.

20. The 2,2-(diaryl) phosphine compound according to any of claims 7–18, wherein at least one of $R^4$ and $R^5$, and $R^6$ and $R^7$ are joined to form a member independently selected from the group consisting of —OCH$_2$O—, benzene, —(CH$_2$)$_4$— and —(CH$_2$)$_3$—.

* * * * *

UNITED STATES PATENT AND TRADEMARK OFFICE
CERTIFICATE OF CORRECTION

PATENT NO. : 6,455,720 B1
DATED : September 24, 2002
INVENTOR(S) : Ken Suzuki et al.

It is certified that error appears in the above-identified patent and that said Letters Patent is hereby corrected as shown below:

Title page, Item [54] and Column 1, line 1,
"2,2(DIARLYL)" should read -- 2,2-(DIARYL) --.
Item [56], FOREIGN PATENT DOCUMENTS, "61022034" shoud read -- 61-22034 --.
OTHER PUBLICATIONS, after "CA:120:245289": "pp. 1257-52" should read -- pp. 1247-52 --.

Column 2,
Lines 6-7, ". As a result, it has been found that" should read -- resulting in --.

Column 3,
Line 8, "formula (2)" should read -- formula (2): --;
Line 18, "(2)" should read -- (2): --; and
Line 53, "and different" should read -- or different --.

Column 17,
Line 66, "caused" should read -- subjected --.

Column 22,
Line 54, "dichlorotetraamminepalladium(II)," should read -- dichlorotetraaminepalladium (II), --.

Column 23,
Line 55, "2-chlorop-" should read -- 2-chloro-p --.

Column 24,
Line 10, "5-iodom-xylene," should read -- 5-iodo-m-xylene, --;
Line 11, "1-iodo-4(trifluoromethoxy)benzene," should read -- 1-iodo-4-(trifluoromethoxy)benzene, --; and
Line 36, "1-fluoro4-methylnaphthalene," should read -- 1-fluoro-4-methylnaphthalene," --.

Column 25,
Line 46, "-mxylene," should read -- -m-xylene --.

Column 26,
Line 66, "mfluoroaniline," should read -- m-fluoroaniline, --.

Column 28,
Line 5, "per" should read -- per mol --.

UNITED STATES PATENT AND TRADEMARK OFFICE
CERTIFICATE OF CORRECTION

PATENT NO. : 6,455,720 B1
DATED : September 24, 2002
INVENTOR(S) : Ken Suzuki et al.

It is certified that error appears in the above-identified patent and that said Letters Patent is hereby corrected as shown below:

Column 31,
Line 67, "2-bromo-$1_1$-" should read -- 2-bromo-1,- --.

Column 33,
Line 22, "7.187.49" should read -- 7.18-7.49 --.

Column 36,
Line 13, "$^{31}$p-NMR" should read -- $^{31}$P-NMR --;
Line 20, "41 ML" should read -- 47 mL --; and
Line 58, "-1(dicyclohexylphosphino)" should read -- -1-(dicyclohexylphosphino) --.

Column 38,
Line 22, "J 2.9 Hz," should read -- J = 2.9 Hz, --.

Column 39,
Line 63, "H-NRM" should read -- $^1$H-NMR --.

Column 40,
Line 42, "Table 18." should read -- Table 18.¶TABLE 18. --.

Column 45,
Line 6, "2(dicyclohexylphosphino)" should read -- 2-(dicyclohexylphosphino) --.

Column 47,
Line 63, "Example 35" should read -- EXAMPLE 35 --.

Column 48,
Line 36, "Example 36" should read -- EXAMPLE 36 --;
Line 50, "Example 37" should read -- EXAMPLE 37 --; and
Line 63, "chomatography" should read -- chromatography --.

Column 49,
Line 1, "Example 38" should read -- EXAMPLE 38 --.
Line 15, "chomatography" should read -- chromatography --.

UNITED STATES PATENT AND TRADEMARK OFFICE
CERTIFICATE OF CORRECTION

PATENT NO. : 6,455,720 B1
DATED : September 24, 2002
INVENTOR(S) : Ken Suzuki et al.

It is certified that error appears in the above-identified patent and that said Letters Patent is hereby corrected as shown below:

Column 50,
Line 16, "animation" should read -- amination --; and
Lines 25 and 42, "formula (2)" should read -- formula (2): --.

Signed and Sealed this

Eleventh Day of March, 2003

JAMES E. ROGAN
*Director of the United States Patent and Trademark Office*